(12) United States Patent
Cajamarca et al.

(10) Patent No.: US 9,913,961 B2
(45) Date of Patent: Mar. 13, 2018

(54) FLEXIBLE CATHETER SHAFT AND METHOD OF MANUFACTURE

(71) Applicant: St. Jude Medical, Cardiology Division, Inc., St. Paul, MN (US)

(72) Inventors: Tobias Cajamarca, Plymouth, MN (US); Gregory James Dakin, Edina, MN (US); Jeffrey John Strong, Coon Rapids, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 14/510,240

(22) Filed: Oct. 9, 2014

(65) Prior Publication Data

US 2015/0119859 A1  Apr. 30, 2015

Related U.S. Application Data

(60) Provisional application No. 61/985,736, filed on Apr. 29, 2014, provisional application No. 61/895,167, filed on Oct. 24, 2013.

(51) Int. Cl.
*A61M 25/00* (2006.01)
*A61B 18/14* (2006.01)
*A61B 18/00* (2006.01)

(52) U.S. Cl.
CPC ..... *A61M 25/0054* (2013.01); *A61B 18/1492* (2013.01); *A61M 25/005* (2013.01);
(Continued)

(58) Field of Classification Search
CPC .......... A61M 25/0045; A61M 25/0051; A61M 25/0012; A61M 25/0013; A61M 25/005;
(Continued)

(56) References Cited

U.S. PATENT DOCUMENTS 3,650,277 A  3/1972  Sjostrand et al.
4,658,819 A  4/1987  Harris et al.
(Continued)

FOREIGN PATENT DOCUMENTS

WO  97/45157  12/1997
WO  00/66020  11/2000
(Continued)

OTHER PUBLICATIONS

Anonymous: "Braid Reinforced Polyimide Tubing", MicroLumen, XP002735901, Retrieved from the Internet: URL: http://www.microlumen.com/medical-tubing/braid-reinforced; retrieved on Feb. 9, 2015.
(Continued)

*Primary Examiner* — Kevin C Sirmons
*Assistant Examiner* — Tiffany Legette-Thompson
(74) *Attorney, Agent, or Firm* — Armstrong Teasdale LLP

(57) ABSTRACT

The present disclosure provides a strong, flexible catheter shaft for use in a catheter system. The flexible catheter shaft includes a braided polyimide tube including one or more outer layers of material of varying flexibility. The flexible catheter shaft provides a shaft having sufficient stiffness and kink resistance to allow an operator to advance an electrode basket connected to the flexible catheter shaft through a guide catheter to a target ablation site without causing vessel trauma. The distal tip of the flexible catheter shaft is designed to have sufficient flexibility to reduce any risk of kicking out a guide catheter when tracking the electrode basket around turns into side branches or bifurcations in the vasculature of a patient and includes a distal spring coil.

8 Claims, 20 Drawing Sheets

(52) U.S. Cl.
CPC .... *A61M 25/0012* (2013.01); *A61M 25/0045* (2013.01); *A61M 25/0052* (2013.01); *A61B 2018/00511* (2013.01); *A61B 2018/00577* (2013.01); *A61M 2205/0266* (2013.01); *Y10T 29/49817* (2015.01)

(58) Field of Classification Search
CPC ...... A61M 25/0054; A61M 2025/1088; A61M 2205/0266; A61M 25/0052; A61B 18/1492; A61B 18/14; A61B 2018/00511; A61B 2018/00577; Y10T 29/49817
USPC .................. 604/527, 528, 523, 524, 530
See application file for complete search history.

(56) References Cited

U.S. PATENT DOCUMENTS

| | | |
|---|---|---|
| 5,035,694 A | 7/1991 | Kasprzyk et al. |
| 5,255,679 A | 10/1993 | Imran |
| 5,300,068 A | 4/1994 | Rosar et al. |
| 5,368,591 A | 11/1994 | Lennox et al. |
| 5,387,233 A | 2/1995 | Alferness et al. |
| 5,465,717 A | 11/1995 | Imran et al. |
| 5,531,779 A | 7/1996 | Dahl et al. |
| 5,598,848 A | 2/1997 | Swanson et al. |
| 5,607,462 A | 3/1997 | Imran |
| 5,628,313 A | 5/1997 | Webster, Jr. |
| 5,676,662 A | 10/1997 | Fleischhacker et al. |
| 5,707,400 A | 1/1998 | Terry, Jr. et al. |
| 5,769,077 A | 6/1998 | Lindegren |
| 5,772,590 A | 6/1998 | Webster, Jr. |
| 5,893,885 A | 4/1999 | Webster, Jr. |
| 5,897,553 A | 4/1999 | Mulier et al. |
| 5,954,649 A | 9/1999 | Chia et al. |
| 5,954,719 A | 9/1999 | Chen et al. |
| 6,004,269 A | 12/1999 | Crowley et al. |
| 6,012,457 A | 1/2000 | Lesh |
| 6,016,437 A | 1/2000 | Tu et al. |
| 6,024,740 A | 2/2000 | Lesh et al. |
| 6,073,048 A | 6/2000 | Kieval et al. |
| 6,096,037 A | 8/2000 | Mulier et al. |
| 6,117,101 A | 9/2000 | Diederich et al. |
| 6,161,543 A | 12/2000 | Cox et al. |
| 6,178,349 B1 | 1/2001 | Kieval |
| 6,200,312 B1 | 3/2001 | Zikorus et al. |
| 6,216,043 B1 * | 4/2001 | Swanson ............... A61B 5/0422 600/374 |
| 6,216,044 B1 | 4/2001 | Kordis |
| 6,233,491 B1 | 5/2001 | Kordis et al. |
| 6,283,951 B1 | 9/2001 | Flaherty et al. |
| 6,287,608 B1 | 9/2001 | Levin et al. |
| 6,292,695 B1 | 9/2001 | Webster, Jr. et al. |
| 6,322,559 B1 | 11/2001 | Daulton et al. |
| 6,460,545 B2 | 10/2002 | Kordis |
| 6,520,983 B1 * | 2/2003 | Colgan ................... A61F 2/90 623/1.11 |
| 6,522,926 B1 | 2/2003 | Kieval et al. |
| 6,613,045 B1 | 9/2003 | Laufer et al. |
| 6,616,624 B1 | 9/2003 | Kieval |
| 6,635,054 B2 | 10/2003 | Fjield et al. |
| 6,656,174 B1 | 12/2003 | Hedge et al. |
| 6,669,655 B1 | 12/2003 | Acker et al. |
| 6,699,231 B1 | 3/2004 | Sterman et al. |
| 6,709,706 B2 * | 3/2004 | Zhong ................... A61L 29/085 427/333 |
| 6,748,255 B2 | 6/2004 | Fuimaono et al. |
| 6,805,131 B2 | 10/2004 | Kordis |
| 6,845,267 B2 | 1/2005 | Harrison et al. |
| 6,954,977 B2 | 10/2005 | Maguire et al. |
| 6,970,730 B2 | 11/2005 | Fuimaono et al. |
| 7,122,031 B2 | 10/2006 | Edwards et al. |
| 7,149,574 B2 | 12/2006 | Yun et al. |
| 7,155,284 B1 | 12/2006 | Whitehurst et al. |
| 7,162,303 B2 | 1/2007 | Levin et al. |
| 7,245,955 B2 | 7/2007 | Rashidi |
| 7,291,146 B2 | 11/2007 | Steinke et al. |
| 7,363,076 B2 | 4/2008 | Yun et al. |
| 7,419,486 B2 | 9/2008 | Kampa |
| 7,465,288 B2 | 12/2008 | Dudney et al. |
| 7,468,062 B2 | 12/2008 | Oral et al. |
| 7,481,803 B2 | 1/2009 | Kesten et al. |
| 7,653,438 B2 | 1/2010 | Deem et al. |
| 7,717,948 B2 | 5/2010 | Demarais et al. |
| 7,742,795 B2 | 6/2010 | Stone et al. |
| 7,850,685 B2 | 12/2010 | Kunis et al. |
| 7,949,407 B2 | 5/2011 | Kaplan et al. |
| 8,145,316 B2 | 3/2012 | Deem et al. |
| 8,224,416 B2 | 7/2012 | de la Rama et al. |
| 8,343,213 B2 | 1/2013 | Salahieh et al. |
| 8,347,891 B2 | 1/2013 | Demarais et al. |
| 8,442,639 B2 | 5/2013 | Walker et al. |
| 8,454,594 B2 | 6/2013 | Demarais et al. |
| 8,545,495 B2 | 10/2013 | Scheib |
| 9,022,948 B2 | 5/2015 | Wang |
| 2002/0068885 A1 | 6/2002 | Harhen et al. |
| 2002/0120304 A1 | 8/2002 | Mest |
| 2002/0133141 A1 * | 9/2002 | Sparks ............... A61M 25/0043 604/523 |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0114739 A1 | 6/2003 | Fuimaono et al. |
| 2003/0216792 A1 | 11/2003 | Levin et al. |
| 2003/0233099 A1 | 12/2003 | Danaek et al. |
| 2004/0215186 A1 | 10/2004 | Cornelius et al. |
| 2005/0234425 A1 * | 10/2005 | Miller ............... A61B 17/3478 604/508 |
| 2005/0288730 A1 | 12/2005 | Deem et al. |
| 2006/0089678 A1 | 4/2006 | Shalev |
| 2007/0135875 A1 | 6/2007 | Demarais et al. |
| 2008/0009831 A1 * | 1/2008 | Griffin ................ A61M 25/005 604/531 |
| 2008/0255478 A1 | 10/2008 | Burdette |
| 2008/0312637 A1 * | 12/2008 | Miller ............... A61B 17/3472 604/512 |
| 2008/0312681 A1 | 12/2008 | Ansel et al. |
| 2009/0076409 A1 | 3/2009 | Wu et al. |
| 2010/0016762 A1 | 1/2010 | Thapliyal et al. |
| 2010/0094209 A1 | 4/2010 | Drasler et al. |
| 2010/0168737 A1 | 7/2010 | Grunewald |
| 2010/0249773 A1 | 9/2010 | Clark et al. |
| 2010/0268307 A1 | 10/2010 | Demarais et al. |
| 2010/0286684 A1 | 11/2010 | Hata et al. |
| 2011/0004087 A1 | 1/2011 | Fish et al. |
| 2011/0054287 A1 * | 3/2011 | Schultz ............... A61B 5/0422 600/374 |
| 2011/0118726 A1 | 5/2011 | de la Rama et al. |
| 2011/0137298 A1 | 6/2011 | Nguyen et al. |
| 2011/0160720 A1 | 6/2011 | Johnson |
| 2011/0213231 A1 | 9/2011 | Hall et al. |
| 2011/0257641 A1 | 10/2011 | Hastings et al. |
| 2011/0264011 A1 | 10/2011 | Wu et al. |
| 2011/0264086 A1 | 10/2011 | Ingle |
| 2011/0282288 A1 * | 11/2011 | Drewes, Jr. ........ A61M 25/0012 604/171 |
| 2012/0143097 A1 | 6/2012 | Pike, Jr. |
| 2012/0143298 A1 | 6/2012 | Just et al. |
| 2012/0296232 A1 | 11/2012 | Ng |
| 2012/0310085 A1 * | 12/2012 | Herweck ........... A61M 25/0023 600/434 |
| 2012/0323233 A1 | 12/2012 | Maguire et al. |
| 2013/0116737 A1 | 5/2013 | Edwards et al. |
| 2013/0131743 A1 | 5/2013 | Yamasaki et al. |
| 2013/0144251 A1 | 6/2013 | Sobotka |
| 2013/0172715 A1 | 7/2013 | Just et al. |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |

(56) References Cited

FOREIGN PATENT DOCUMENTS

| WO | 2007/149970 | 12/2007 |
|---|---|---|
| WO | 2008/141150 | 11/2008 |
| WO | 2008/151001 | 12/2008 |
| WO | 2012/064818 | 5/2012 |
| WO | 2012/106492 | 8/2012 |
| WO | 2013146306 | 10/2013 |

OTHER PUBLICATIONS

International Search Report and Written Opinion for Application No. PCT/US2014/059817 dated Mar. 13, 2015.
Abboud, Francois M., The Sympathetic System in Hypertension, State-of-the-Art Review, Hypertension Journal of the American Heart Association, Hypertension 4 (suppl II): II-208-II-225, 1982.
Allen, Edgar V., Sympathectomy for Essential Hypertension, Circulation Journal of the American Heart Association, vol. VI, Jul. 1952, 131-140.
Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.
Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6(2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of the American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.

Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review—Part II, Journal of the National Medical Association, May 1948, vol. 40, No. 3., 113-116.
Dailey, U.G., Surgical Treatment of Hypertension: A Review—Part III, Journal of the National Medical Association, Jul. 1948, vol. 40, No. 4, 160-162.

(56) References Cited

OTHER PUBLICATIONS

Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension A Systematic Review and Meta-Analysis, Journal of the American College of Cardiology, vol. 62, No. 3, 2013, 231-241.
De Wardener, H.E., The Hypothalamus and Hypertension, Physiological Reviews,vol. 81, No. 4, Oct. 2001.
Dequattro V. et al, The Sympathetic Nervous System: The Muse of Primary Hypertension, Journal of Human Hypertension, 2002, 16 (Supp) 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of The American Heart Association, vol. 13, No. 6, Part 1, Jun. 1989, 539-548.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of The American Heart Association, vol. 41, Mar. 2003, Part II, 621-624.
Dibona, Gerald F., Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of The American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of The American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.

Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:I-13 (1982).
Grassi, Guido et al, Baroreflex Control of Sympathetic Nerve Activity in Essential and Secondary Hypertension, Hypertension Journal of The American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 Pt 2):F738-F745.
Hoobler, S.W. et al, The Effects of Splanchnicectomy on the Blood Pressure in Hypertension, Circulation Journal of The American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6(4):270-6.

(56) References Cited

OTHER PUBLICATIONS

Howard, James P. et al, Size of Blood Pressure Reduction from Renal Denervation: Insights from Meta-Analysis of Antihypertensive Drug Trials of 4121 Patients with Focus on Trial Design: the CONVERGE Report, Heart 2013;0:1-9.
Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.
Howell, Marcus H. et al, Tandem Stenting of Crossed Renal Arteries with Ostial Stenosis, Tex Heart Inst J. 2000; 27(2): 166-169.
Hoye, Neil A. et al, Endovascular Renal Denervation: A Novel Sympatholytic with Relevance to Chronic Kidney Disease, Clinical Kidney Journal Advance Access, (2013) 0: 1-8.
Huang, Shoei K. Stephen et al, Radiofrequency Catheter Ablation of Cardiac Arrhythmias, Basic Concepts and Clinical Applications, Wiley-Blackwell, Jun. 2000, 1-12.
Huang, Wann-Chu, Renal Denervation Prevents and Reverses Hyperinsulinemia-Induced Hypertension in Rats, Hypertension Journal of The American Heart Association, 1998;32:249-254.
Humpreys, Michael H., Renal Nerves and CKD: Is Renal Denervation the Answer?, Journal of The American Socity of Nephrology, 2012, 23: 1-3.
International Search Report and Written Opinion for Application No. PCT/US2010/054637 dated Jan. 3, 2011.
International Search Report and Written Opinion for Application No. PCT/US2010/054684 dated Jan. 10, 2011.
Irigoyen, M.C.C. et al, Baroreflex Control of Sympathetic Activity in Experimental Hypertension, Brazilian Journal of Medical and Biological Research, (1998) 31: 1213-1220.
Izzo, Jr, Joseph L. et al, The Sympathetic Nervous System and Baroreflexes in Hypertension and Hypotension, Current Hypertension Reports 1999, 3:254-263.
Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19/26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the Symplicity HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, GE et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.
Labeit, Alexander Michael et al, Changes in the Prevalence, Treatment and Control of Hypertension in Germany? A Clinical-Epidemiological Study of 50.000 Primary Care Patients, PLOS One, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.
Lambert, Gavin W. et al, Health-Related Quality of Life After Renal Denervation in Patients With Treatment-Resistant Hypertension, Hypertension. 2012;60:1479-1484.
Lee, Sang Joon et al, Ultrasonic Energy in Endoscopic Surgery, Yonsei Medical Journal, vol. 40, No. 6, pp. 545-549, 1999.
Leertouwer, Trude C. et al, In-Vitro Validation, with Histology, of Intravascular Ultrasound in Renal Arteries, Journal of Hypertension 1999, vol. 17 No. 2, 271-277.

(56) References Cited

OTHER PUBLICATIONS

Leishman, A.W.D., Hypertension—Treated and Untreated, British Medical Journal, May 1959, 1361-1368.

Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.

Levin, Stephen, Ardian: Succeeding Where Drugs Fail Treating Hypertension in the Cath Lab, In Vivo: The Business & Medicine Report, vol. 27, No. 10, Nov. 2009.

Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.

Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.

Luscher, Thomas F. et al, Renal Nerve Ablation After Symplicity HTN-3: Confused at the Higher Level?; European Heart Journal, doi:10.1093/eurheartyehu195; May 14, 2014.

Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 (May/Jun. 1999): pp. 481-498.

Mahfoud, Felix et al, Expert Consensus Document from the European Society of Cardiology on Catheter-Based Renal Denervation, European Heart Journal, Jul. 2013;34(28):2149-57.

Mancia, Giuseppe et al, Sympathetic Activation in the Pathogenesis of Hypertension and Progression of Organ Damage, Hypertension Journal of The American Heart Association, 1999, 34:724-728.

McGahan, John P. et al, History of Ablation, Tumor Ablation, 2005, pp. 3-16.

Medtronic, Inc., J.P. Morgan Healthcare Conference, Corrected Transcript, Jan. 13, 2014, Factset:Callstreet, www.callstreet.com.

Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.

Medtronic, Inc., RDN Therapy with the Symplicity Renal Denervation System, Procedure Fact Sheet, www.medtronic.com, 2011.

Medtronic, Inc., Renal Denervation (RDN) Novel Catheter -based Treatment for Hypertension, Symplicity RDN System Common Q&A, 2011.

Medtronic, Inc., Scientific Basis Behind Renal Denervation for the Control of Hypertension, Dec. 2012, http://www.icimeeting.com/2012/images/stories/PDF/1448_Wilcox_I_Mon.pdf.

Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.

Meredith, I T et al, Exercise Training Lowers Resting Renal But Not Cardiac Sympathetic Activity in Humans; Hypertension Journal of The American Heart Association, 1991;18:575-582.

Michaelis, Lawrence L. et al, Effects of Renal Denervation and Renin Depletion on the Renal Responses to Intravascular Volume Expansion, Ann Surg. Mar. 1972; 175(3): 424-430.

Millard, F.C. et al, Renal Embolization for Ablation of Function in Renal Failure and Hypertension, Postgraduate Medical Journal (1989) 65, 729-734.

Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.

Mogil, Robert A. et al, Renal Innervation and Renin Activity in Salt Metabolism and Hypertension, American Journal of Physiology, vol. 216, No. 4, Apr. 1969, 693-697.

Morita, Hironobu et al, Neural Control of Urinary Sodium Excretion During Hypertonic NaC1 Load in Conscious Rabbits: Role of Renal and Hepatic Nerves and Baroreceptors, Journal of the Autonomic Nervous System, 34 (1991) 157-170.

Morrissey, D.M. et al, Sympathectomy in the Treatment of Hypertension, The Lancet, Feb. 1953, 403-408.

Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.

Moss, Jonathan, Interventional Radiology and Renal Denervation, Interventions, vol. 13, Issue 3, 2013.

Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).

Naidoo, N. et al, Thoracic Splanchnic Nerves: Implications for Splanchnic Denervation, Journal of Anatomy, Nov. 2001;199(Pt 5):585-590.

Nakagawa, A. et al, Selective Ablation of Porcine and Rabbit Liver Tissue Using Radiofrequency: Preclinical Study, European Surgical Research, 1999;31:371-379.

Nakagawa, Hiroshi et al, Inverse Relationship Between Electrode Size and Lesion Size During Radiofrequency Ablation With Active Electrode Cooling, Circulation. Aug. 4, 1998;98(5):458-465.

Nanni, Gregg S. et al, Control of Hypertension by Ethanol Renal Ablation, Radiology 148: 51-54, Jul. 1983.

Ndegwa, S., Catheter-Based Renal Denervation for Treatment-Resistant Hypertension [Issues in emerging health technologies issue 121]. Ottawa: Canadian Agency for Drugs and Technologies in Health; 2013.

Neutel, Joel M., Hypertension and Its Management: A Problem in Need of New Treatment Strategies, Journal of Renin-Angiotensin-Aldosterone System 2000 1: S10-S13.

Newcombe, C.P. et al, Sympathectomy for Hypertension, British Medical Journal, Jan. 1959, 142-144.

Ng, Fu Siong et al, Catheter Ablation of Atrial Fibrillation, Clinical Cardiology, 25, 384-394 (2002).

Norman, Roger A. et al, Role of the Renal Nerves in One-Kidney, One Clip Hypertension in Rats, Hypertension Journal of The American Heart Association, 1984;6:622-626.

Nozawa, Takashi et al, Effects of Long-Term Renal Sympathetic Denervation on Heart Failure After Myocardial Infarction in Rats, Heart Vessels (2002) 16:51-56.

O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.

O'Hagen, Kathleen P. et al, Renal Denervation Decreases Blood Pressure in DOCA-Treated Miniature Swine With Established Hypertension, American Journal of Hypertension, 1990; 3:62-64.

Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.

Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.

Oparil, Suzanne et al, Renal Nerve Ablation: Emerging Role in Therapeutics; Blood Pressure, Oct. 2011, vol. 20, No. 5, pp. 253-255.

Oral, Hakan et al, Pulmonary Vein Isolation for Paroxysmal and Persistent Atrial Fibrillation, Circulation Journal of The American Heart Association, 2002;105:1077-1081.

Osborn, Jeffrey L. et al, Long-Term Increases in Renal Sympathetic Nerve Activity and Hypertension, Clinical and Experimental Pharmacology and Physiology (1997) 24,72-76.

Osborn, John W., The Sympathetic Nervous System and Long-Term Regulation of Arterial Pressure: What Are the Critical Questions?, Clinical and Experimental Pharmacology and Physiology (1997) 24, 68-71.

Ou, Baiqing et al, Baroreflex Sensitivity Predicts the Induction of Ventricular Arrhythmias by Cesium Chloride in Rabbits, Japanese Circulation Journal, 1999; 63: 783-788.

Oz, Mehmet, Pressure Relief, Time Magazine, Monday, Jan. 9, 2012.

(56) References Cited

OTHER PUBLICATIONS

Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14(4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, 10-15, Jan. 2002.
Pearce, John A. et al, Blood Vessel Architectural Features and Their Effect on Thermal Phenomena, Critical Reviews, vol. CR75, Bellingham, WA: SPIE Optical Engineering Press; 2000, p. 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3):139-142.
Persu, Alexandre et al, Renal Denervation: Ultima Ratio or Standard in Treatment-Resistant Hypertension, Hypertension Journal of The American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.
Plouin, Pierre-Francois et al, Blood Pressure Outcome of Angioplasty in Atherosclerotic Renal Artery Stenosis A Randomized Trial, Hypertension Journal of The American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System An Overview of Structure and Function, Journal of Pharmacological and Toxicological Methods 44 (2000) 333-340.
Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.

Yamada, Yutaka et al, Age-Related Changes in Muscle Sympathetic Nerve Activity in Essential Hypertension, Hypertension Journal of The American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.
Zazgornik, Jan et al, Bilateral Nephrectomy: The Best, but Often Overlooked, Treatment for Refractory Hypertension in Hemodialysis Patients, AJH 1998; 11:1364-1370.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.
Robbins, Ivan M. et al, Pulmonary Vein Stenosis After Catheter Ablation of Atrial Fibrillation, Circulation Journal of The American Heart Association, 1998;98:1769-1775.
Rocha-Singh, Krishna J., Catheter-Based Sympathetic Renal Denervation A Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4):94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of The American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of The American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.

(56) References Cited

OTHER PUBLICATIONS

Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of The American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following *KSR* V. *Teleflex*, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of The American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. and Exper.-Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.

\* cited by examiner

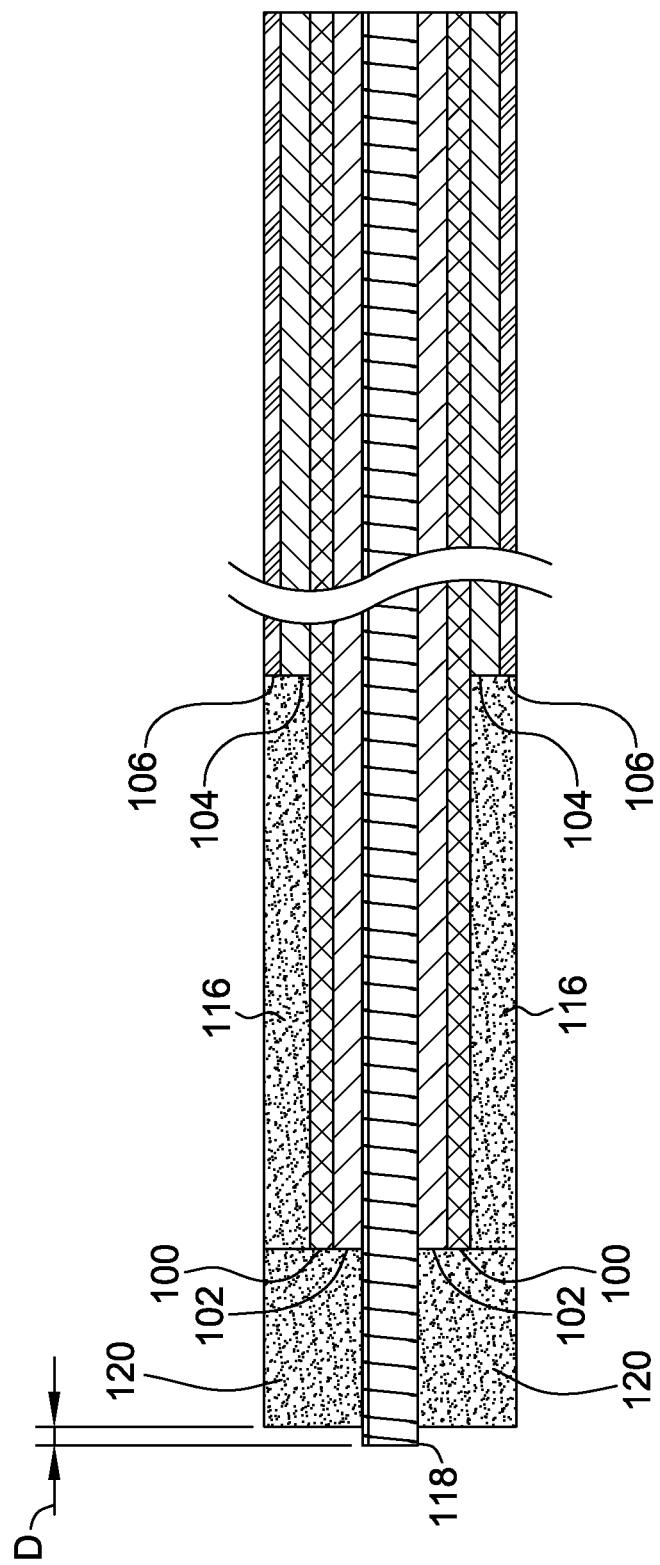

FLEXIBLE CATHETER SHAFT AND METHOD OF MANUFACTURE

CROSS-REFERENCE TO RELATED APPLICATIONS

This application claims priority to provisional application Ser. No. 61/895,167, filed Oct. 24, 2013, and provisional application Ser. No. 61/985,736, filed Apr. 29, 2014, the entire specifications of which are incorporated herein.

FIELD OF THE DISCLOSURE

The present disclosure relates generally to catheters that are used in the human body. In particular, the present disclosure relates to a flexible catheter shaft including a braided polyimide tube having a modified distal portion, and a spring coil disposed at least partially therein to improve flexibility, kink resistance, column strength, and maneuverability of the flexible catheter shaft. In some embodiments, an additional outer spring coil is introduced onto at least a portion of the spring coil at the distal end to further improve the flexible catheter shaft performance and durability.

BACKGROUND ART

Catheter systems are well known in the art for use in medical procedures, such as diagnostic, therapeutic and ablative procedures. Typical catheter systems generally include an elongate flexible catheter shaft extending from a handle. A physician manipulates the catheter through the patient's vasculature to an intended site within the patient. The catheter typically carries one or more working components, such as electrodes and thermocouples, or other diagnostic, therapeutic or ablative devices for carrying out the procedures. One or more controls or actuators may be provided on the handle for selectively adjusting one or more characteristics of the working components.

Since the path through the patient's vasculature to the intended site is often long and tortuous, steering forces typically must be transmitted over relatively great distances. Accordingly, it is generally desirable for a catheter to have sufficient axial (e.g., column) strength to be pushed through the patient's vasculature via a force applied at its proximal end ("pushability"). It is also generally desirable for a catheter to transmit a torque applied at the proximal end to the distal end ("torqueability"). Pushability and torqueability (collectively, "maneuverability") permit an operator, such as a physician, to manipulate a catheter to an intended site and then properly orient the catheter during an ablation procedure. It is also generally desirable for a catheter, and specifically the catheter tip, to have sufficient flexibility to substantially conform to the patient's vasculature and yet resist kinking as it does so. Kinking is often the result of a localized failure of the material of the catheter when localized stresses exceed the yield strength of the material.

To provide the desired pushability, torqueability, flexibility, and kink resistance, many catheter shafts are made at least partially of thermoplastic polymer materials that may be reinforced with a secondary material. The desirable characteristics of pushability, torqueability, flexibility, and kink resistance are often in tension or conflict with one another, however, with improvements in one requiring compromises in another.

BRIEF SUMMARY OF THE DISCLOSURE

In one embodiment, the present disclosure is directed to a catheter shaft comprising a braided polyimide tube having a proximal portion and a distal portion, a substrate layer disposed within the braided polyimide tube, a spring coil disposed within the substrate layer and including a section extending past a distal end of the distal portion of the braided polyimide tube, and an outer spring coil disposed over at least a portion of the section of the spring coil extending past the distal end of the distal portion of the braided polyimide tube. The proximal portion of the braided polyimide tube is covered by a first coating and the distal portion of the braided polyimide tube and the outer spring coil is covered by a second coating. A pocket extends past a distal end of the outer spring coil.

In another embodiment, the present disclosure is directed to a catheter shaft comprising a braided polyimide tube having a proximal portion and a distal portion, a polytetrafluoroethylene/polyimide composite layer disposed within the braided polyimide tube, a spring coil disposed within the polytetrafluoroethylene/polyimide composite layer and including a section extending past a distal end of the braided polyimide tube, and an outer spring coil disposed over at least a portion of the section of the spring coil extending past the distal end of the distal portion of the braided polyimide tube. The proximal portion of the braided polyimide tube is covered by a first layer of polyimide and a second layer of polyether block amide and the distal portion of the braided polyimide tube and the outer spring coil is covered by a layer of polyether block amide. A pocket comprised of a polyether block amide extends past a distal end of the outer spring coil.

In another embodiment, the present disclosure is directed to a method of manufacturing a catheter shaft, the method comprising providing a braided polyimide tube having at least one layer disposed on top of the tube and having a substrate layer disposed within the braided polyimide tube; removing from a distal portion of the braided polyimide tube the at least one layer; introducing a new layer of material onto the distal portion of the braided polyimide tube; introducing a spring coil inside of the substrate layer wherein a section of the spring coil extends beyond a distal end of the braided polyimide tube; introducing an outer spring coil onto at least a portion of the spring coil that extends beyond a distal end of the braided polyimide tube; introducing a layer of material onto the outer spring coil; and forming a pocket on a distal end of the outer spring coil.

In another embodiment, the present disclosure is directed to a catheter shaft comprising a braided polyimide tube having a proximal portion and a distal portion, a substrate layer disposed within the braided polyimide tube, and a spring coil disposed within the substrate layer and including a section extending past a distal end of the distal portion of the braided polyimide tube. The proximal portion of the braided polyimide tube is covered by a first coating and the distal portion of the braided polyimide tube is covered by a second coating. The section of the spring coil that extends past the distal end of the braided polyimide tube is covered by a third coating, and a pocket extends past a distal end of the spring coil.

In another embodiment, the present disclosure is directed to a catheter shaft comprising a braided polyimide tube having a proximal portion and a distal portion, a polytetrafluoroethylene/polyimide composite layer disposed within the braided polyimide tube, and a spring coil disposed within the polytetrafluoroethylene/polyimide composite layer and including a section extending past a distal end of the braided polyimide tube. The proximal portion of the braided polyimide tube is covered by a first layer of polyimide and a second layer of polyether block amide and the distal portion of the braided polyimide tube is covered by a layer of polyether block amide. The section of the spring coil that extends past the distal end of the braided polyimide tube is covered by a layer of polyether block amide and a pocket comprised of a polyether block amide extends past a distal end of the spring coil.

In another embodiment, the present disclosure is directed to a method of manufacturing a catheter shaft, the method comprising providing a braided polyimide tube having at least one layer disposed on top of the tube and having a substrate layer disposed within the braided polyimide tube; removing from a distal portion of the braided polyimide tube the at least one layer; introducing a new layer of material onto the distal portion of the braided polyimide tube; introducing a spring coil inside of the substrate layer wherein a portion of the spring coil extends beyond a distal end of the braided polyimide tube; introducing a layer of material onto the portion of the spring coil that extends beyond the distal end of the braided polyimide tube; and forming a pocket on a distal end of the spring coil.

The foregoing and other aspects, features, details, utilities and advantages of the present disclosure will be apparent from reading the following description and claims, and from reviewing the accompanying drawings.

BRIEF DESCRIPTION OF THE DRAWINGS

FIGS. 8 and 8A are longitudinal cross-sectional views of the braided polyimide tube of FIG. 7 including additional materials on the spring coil.

Corresponding reference characters indicate corresponding parts throughout the several views of the drawings. It is understood that that Figures are not necessarily to scale.

DETAILED DESCRIPTION OF THE DISCLOSURE

Figure 1:
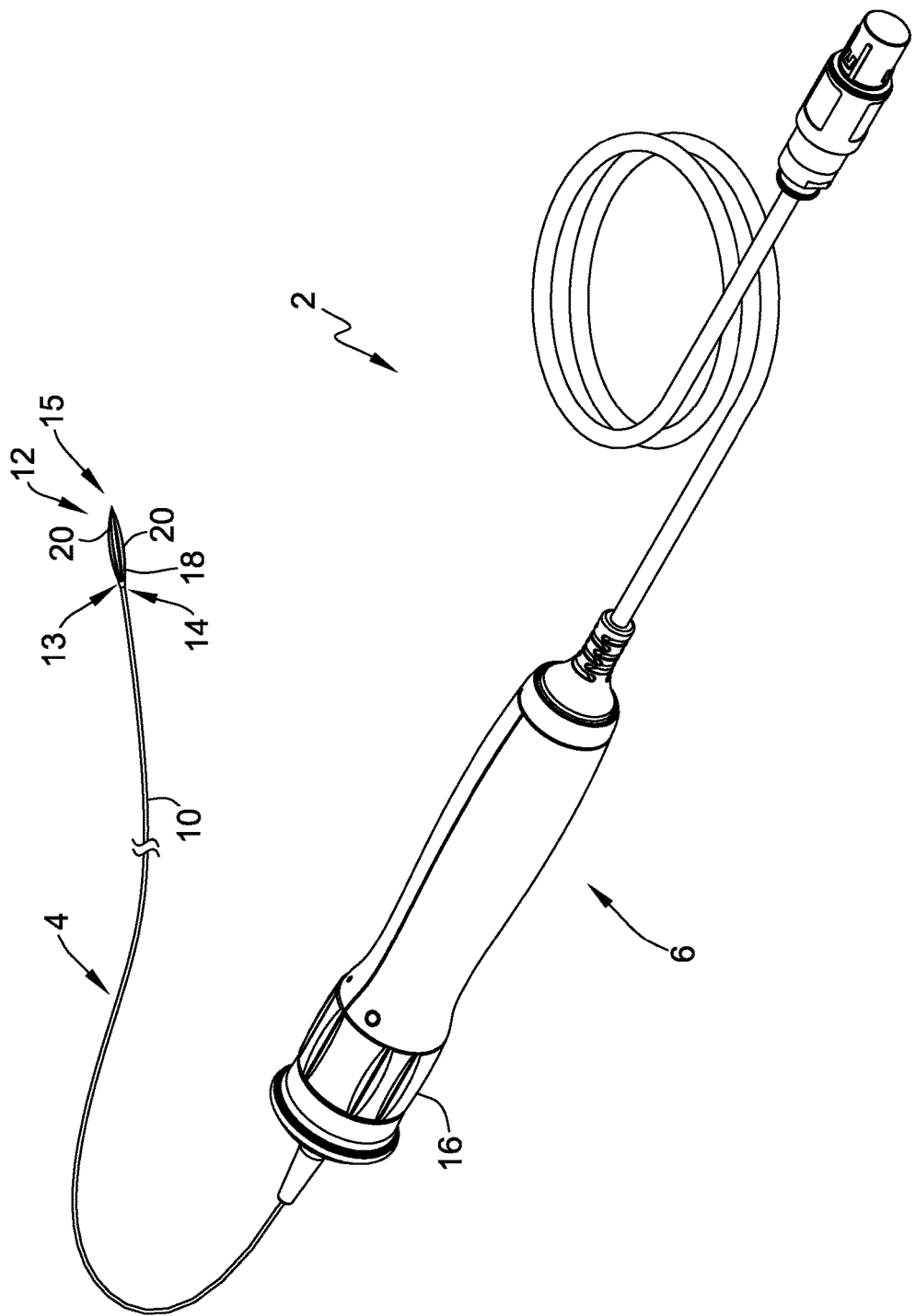
FIG. 1 is a perspective view of one embodiment of a catheter system including a handle, a catheter shaft, and an electrode assembly having multiple electrodes, with the electrode assembly being in a collapsed configuration.

The present disclosure provides a flexible catheter shaft suitable for use in the human vasculature for known medical procedures, such as renal ablation procedures. Catheters utilizing flexible catheter shafts according to the present disclosure advantageously exhibit improved maneuverability, flexibility, and kink resistance. For purposes of this description, the disclosure will be described in connection with an elongate electrophysiology catheter. It is contemplated, however, that the described features and methods may be incorporated into any number of catheters (e.g., steerable catheters, introducer catheters, balloon catheters, bullet catheters, and the like) as would be appreciated by one of ordinary skill in the art based on the disclosure herein.

More specifically, the present disclosure provides a strong, flexible catheter shaft that includes a braided polyimide tube having a spring coil disposed therein that extends past a distal end of the braided polyimide tube. In many embodiments, the strong, flexible catheter shaft further includes an outer spring coil disposed around at least a portion of the spring coil such that the flexible catheter shaft includes two separate spring coils to further improve durability and performance. In many embodiments, a distal portion of the polyimide tube has been modified to include a flexible material, such as a polyether block amide, thereon. Additionally, the surface of the spring coil (or the surface of the outer spring coil in many embodiments) that extends past the distal end of the braided polyimide tube may include one or more materials thereon to improve strength and flexibility, and may further include a pocket sized and configured for receiving at least a portion of a proximal end of an electrode basket. The flexible catheter shaft provides a shaft having sufficient stiffness and kink resistance to allow an operator to advance an electrode basket connected to the flexible catheter shaft through a guide catheter to a target ablation site without causing vessel trauma. The distal tip of the flexible catheter shaft is designed to have sufficient flexibility to reduce any risk of kicking out of a guide catheter when tracking the electrode basket around various turns in the vasculature of a patient. In many embodiments, the flexible catheter shaft may be sized and configured to be used in combination with a 6 French guide catheter (typical inner diameter of about 0.070 inches (about 0.178 centimeters) while still allowing sufficient room between the guide catheter and flexible catheter shaft for a contrast agent to pass therebetween during a procedure.

The flexible catheter shaft of the present disclosure additionally provides sufficient column strength to facilitate the opening of an electrode basket attached thereto through the use of an activation wire that is routed through the interior of the flexible catheter shaft, while maintaining a generally consistent length as it is tracked through a tortuous pathway inside of a patient. Additionally, the flexible catheter shaft provides controllable torque such that the electrode basket attached thereto can easily be rotated 45 degrees or so between ablation cycles, while maintaining a sufficiently large internal diameter to allow for the passage of the activation wire and other electrical wires to the handle of the catheter system.

Figure 2:
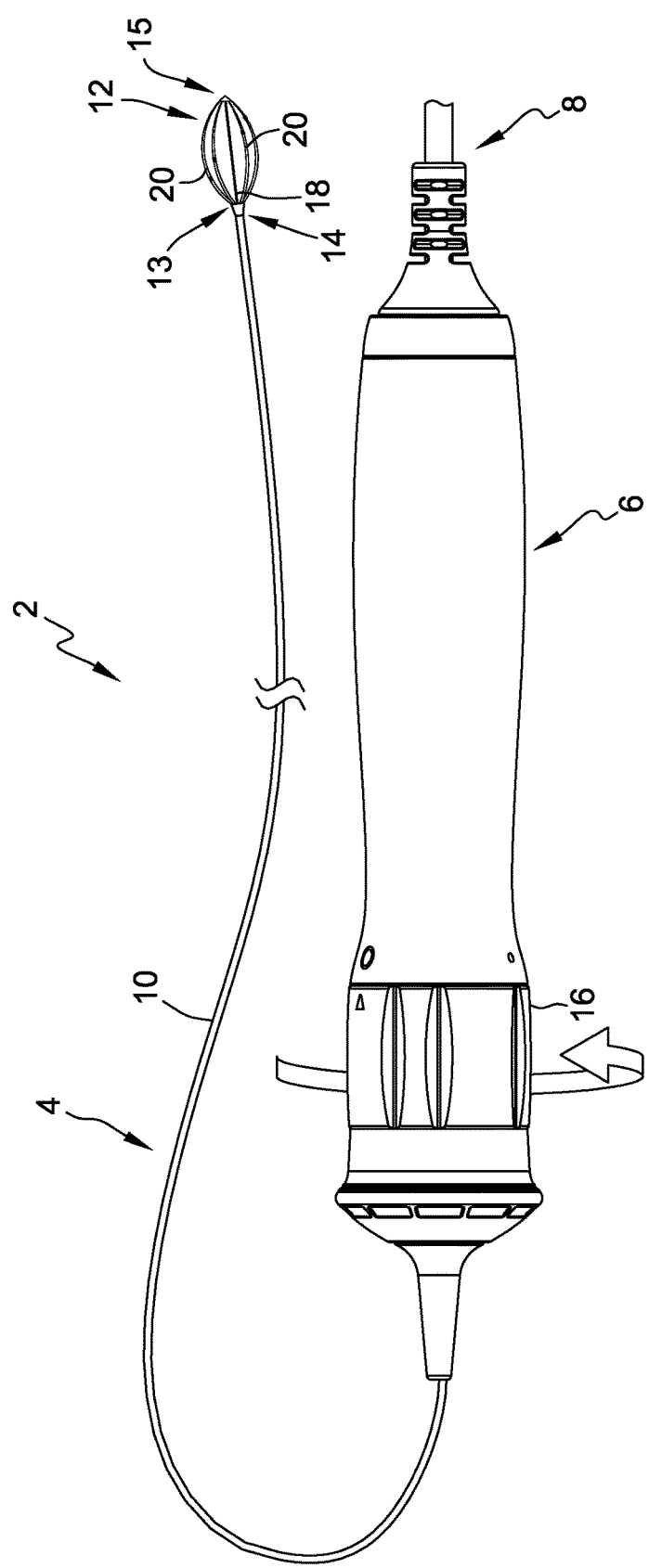
FIG. 2 is a side elevation of the catheter system of FIG. 1, with the electrode assembly being in an expanded configuration resulting from rotation of a rotatable actuator.

Referring now to the drawings, and in particular to FIGS. 1 and 2, a conventional catheter system 2 is shown by way of background and reference. Catheter system 2 includes a flexible catheter 4, a handle 6 to which flexible catheter 4 is connected, and a conductor assembly 8 for electrically connecting catheter system 2 to a suitable power supply (not shown). As one example, catheter system 2 illustrated and described herein is suitably constructed for use as an ablation system, such as a renal or heart ablation system. More particularly, illustrated catheter system 2 is a multi-electrode renal denervation system. One example of such a catheter system 2 is currently made by St. Jude Medical, Inc. under the trade name EnligHTN. General operation of a multi-electrode renal denervation system is known to those of skill in the art and is not described further herein except to the extent necessary to describe the present embodiments. It is also understood that catheter system 2 may be used for any other suitable treatment or purpose without departing from the scope of this disclosure. Additionally, while catheter system 2 is illustrated and described herein as including flexible catheter 4, catheter system 2 may further include other components used, for example, to guide flexible catheter 4 into the patient—such as, without limitation, a relatively more rigid guide catheter (not shown) or guide wire (not shown).

Flexible catheter 4 includes an elongate, flexible hollow shaft 10 connected to handle 6 at or near a proximal or rear end of the catheter shaft (not shown because it is hidden by a connector at the front end of handle 6), and an electrode assembly 12 disposed at or near a distal or front end 14 of flexible hollow shaft 10. Electrode assembly 12 includes proximal end 13 and distal end 15. It is understood, however, that electrode assembly 12 may be disposed anywhere along flexible hollow shaft 10 intermediate the proximal end and the distal end 14 thereof without departing from the scope of this disclosure. As used herein, the terms proximal and front, and distal and rear, are used with reference to the orientation of catheter system 2 illustrated in the various drawings and for the purpose of describing the various embodiments set forth herein, and are not intended as limiting the catheter system and related components to having any particular orientation upon assembly or during operation thereof. In particular, the terms proximal and rear refer to a longitudinal position that is relatively nearer to handle 6 while the terms distal and front refer to a longitudinal position that is relatively farther from handle 6.

Illustrated electrode assembly 12 is in the form of what may be referred to as an electrode basket and includes struts 20, and is suitably configurable between a collapsed configuration (FIG. 1) for maneuvering and positioning the electrode assembly in the patient, and an expanded configuration (FIG. 2) for operation of the electrode assembly to perform a desired procedure such as an ablation procedure. An annular (e.g., ring-shaped) actuator 16 is mounted on handle 6 for rotation relative thereto and is operatively connected to electrode assembly 12 for selectively configuring the electrode assembly between its collapsed and expanded configurations. It is understood that another suitable actuator (e.g., slide, push button, lever, etc.) may be used instead of rotating actuator 16 to selectively configure electrode assembly 12 without departing from the scope of this disclosure. In some embodiments, electrode assembly 12 may be selectively adjustable between an infinite number of configurations (e.g., degrees of expansion) between its collapsed and expanded configurations using actuator 16.

A control line, such as a suitable cable or pull wire 18 extends from electrode assembly 12 within flexible hollow shaft 10 and into the handle 6 for operative connection with the actuator to thereby operatively connect the actuator 16 with electrode assembly 12. In some embodiments two or more pull wires, cables or other suitable control lines or tubes may be used for selectively configuring electrode assembly 12. It is also understood that cable or pull wire 18 (also referred to as a "control line") may be any suitable control line other than a pull wire, such as a cable, string, tie, compression member or other suitable control to operatively connect electrode assembly 12 to actuator 16. A suitable electrical wire bundle (not shown) also extends through flexible hollow shaft 10 from handle 6 to electrode assembly 12 to deliver power to, and receive feedback from, electrode assembly 12.

As noted herein, the flexible catheter shafts of the present disclosure include a braided polyimide tube having a distal portion and a proximal portion, a substrate layer disposed within the interior of the braided polyimide tube, and a spring coil disposed inside of the substrate layer and extending past a distal end of the polyimide tube. The flexible catheter shaft further includes a pocket at a distal end of the spring coil. The proximal portion of the braided polyimide tube is covered by at least one layer, and the distal portion of the polyimide tube is covered by at least one layer that is different than the at least one layer covering the proximal portion. The portion of the spring coil that extends past the distal end of the polyimide tube is also covered by at least one layer. The flexible catheter shaft is sized and configured to be attached at the distal end to a suitable electrode basket (i.e., the electrode basket fits inside of the pocket) and attached at the proximal end to a catheter handle. The layer or layers introduced onto the distal portion of the braided polyimide tube and the layer or layers covering the portion of the spring coil that extends past the distal end of the braided polyimide tube are selected to facilitate the desired flexibility, torqueability and strength of the distal end and tip upon use of the flexible catheter shaft.

The flexible catheter shafts of the present disclosure may be constructed by first selecting a suitable braided polyimide tube. Suitable braided polyimide tubes may be constructed from a braid reinforced polyimide material. The braid is generally in a ribbon pattern, woven pattern, circular woven pattern or the like, and the braid wire used is generally stainless steel. A suitable braid or coil material is 304V stainless steel. Both round and flat wires are within the scope of the present disclosure, with flat wires being desirable in many embodiments. In one particular embodiment, a suitable stainless steel flat braid wire is a 0.001 inch (0.0025 centimeters) by 0.003 inch (0.0076 centimeters) wire. Braided polyimide tubes provide reinforced tubes that may provide increased column strength, torque transmission, and increased burst strength. Suitable braided polyimide tubes for use in the present disclosure are commercially available from MicroLumen (Oldsmar, Fla.).

As noted above, suitable braided polyimide tubes will have a substrate layer or liner disposed therein. Suitable substrate layers or liners may be 0.001 inches (0.003 centimeters) thick, or even 0.002 inches (0.005 centimeters) thick, or even 0.003 inches (0.008 centimeters) thick or more. Suitable substrate layers may be constructed of polyimide, polytetrafluoroethylene, or polytetrafluoroethylene composites, such as a polytetrafluoroethylene/polyimide composite. In many embodiments, a polytetrafluoroethylene/polyimide composite is a desirable substrate material.

Suitable braided polyimide tubes additionally include a first outer layer. The first outer layer may be constructed of a polyimide, a thermoplastic such as a polyether block amide (Pebax®), a nylon, a urethane, or combinations thereof. In many embodiments, a polyimide is a desirable substrate material. First outer layer 104 may be 0.001 inches (0.003 centimeters) thick, or even 0.002 inches (0.005 centimeters) thick, or even 0.003 inches (0.008 centimeters) thick or more. Braided polyimide tubes including a substrate layer and a first outer layer are commercially available from MicroLumen (Oldsmar, Fla.).

Figure 3:
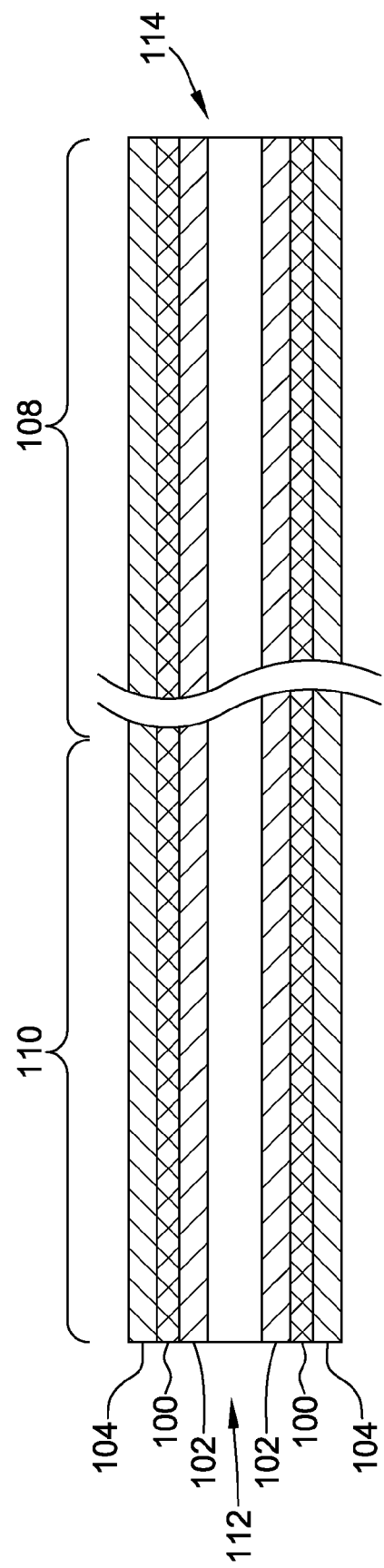
FIG. 3 is a longitudinal cross-sectional view of a braided polyimide tube suitable for use in the present disclosure.

Referring now to FIG. 3, there is shown a suitable braided polyimide tube for preparing a flexible catheter shaft of the present disclosure. Braided polyimide tube 100 includes substrate layer 102 disposed within braided polyimide tube 100 and first outer layer 104. Substrate layer 102 may be, for example, a polytetrafluoroethylene/polyimide composite layer and first outer layer may be, for example, a polyimide layer. Braided polyimide tube 100 also has proximal portion 108, proximal end 114, distal portion 110, and distal end 112.

Once a suitable braided polyimide tube has been selected, such as that described in FIG. 3, the braided polyimide tube is subjected to a reflow or other suitable process to introduce a second outer layer or topcoat of material onto the braided polyimide tube to impart additional flexibility to the braided polyimide tube, and in particular to the proximal end of the braided polyimide tube. The second outer layer also allows for improved reflow adhesion to layers applied in subsequent manufacturing steps, such as those described below, and provides a smooth and lubricious finish to the surface of the braided polyimide tube. The second outer layer covers the first outer layer, and may be constructed of thermoplastics, polystyrene, polyvinyl chloride, ethylene vinyl acetate, polyurethanes (urethane-based materials), nylon, polyimide, polyether block amides (Pebax®), and the like. Other heat settable plastics or superplastics are also suitable and known to those of ordinary skill in the art. Particularly desirable thermoplastic materials for constructing the second outer layer include Pebax® polyether block amides, including those Pebax® materials having a durometer value of about 72 D.

Figure 4:
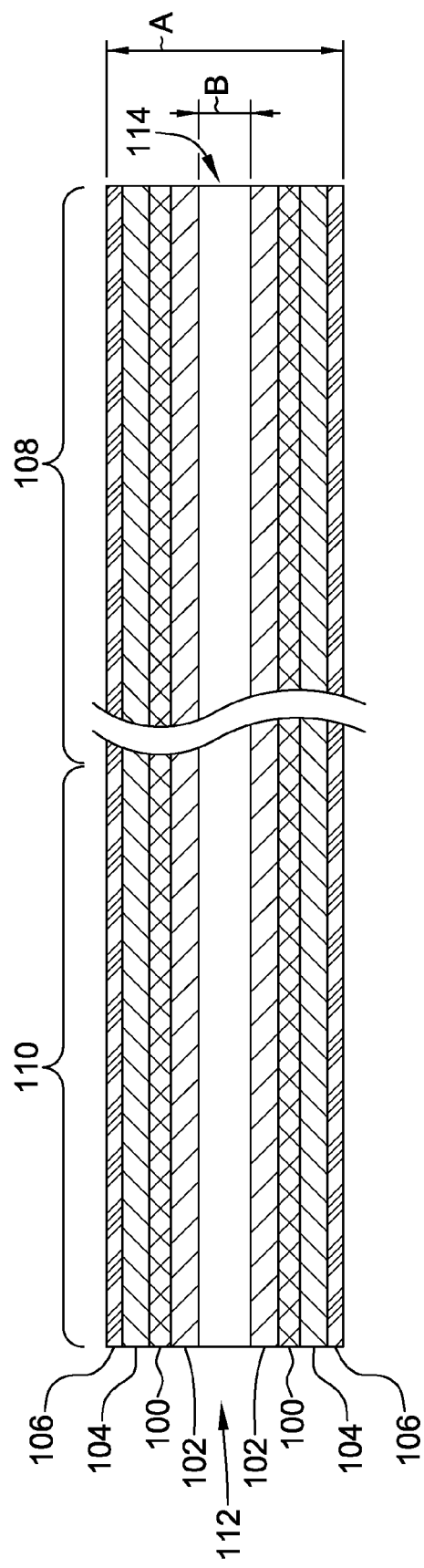
FIG. 4 is a longitudinal cross-sectional view of the braided polyimide tube of FIG. 3 including an additional layer of material.

Once a suitable second outer layer material is selected, it is introduced around the exterior of the braided polyimide tube. In many embodiments, the second outer layer will be formed from a tubular material that is placed around the exterior of the braided polyimide tube (along with a heat shrink material) and subjected to a reflow process. Once the reflow process is complete and the second outer layer formed, the heat shrink material is removed. In other embodiments, the second outer layer may be formed by liquefying a desired material (such as a Pebax® material) and then applying the material. Referring now to FIG. 4, there is shown braided polyimide tube 100 including substrate layer 102 disposed within braided polyimide tube 100 and first outer layer 104. Second outer layer 106 surrounds first outer layer 104. Braided polyimide tube 100, including both first outer layer 104 and second outer layer 106 have an outer diameter A and an inner diameter B. Outer diameter A may generally be less than 0.0620 inches (0.1575 centimeters), or even less than 0.0615 inches (0.1562 centimeters), or even less than 0.0610 inches (0.1549 centimeters). In some embodiments, outer diameter A may be about 0.0600 inches (about 0.1524 centimeters). Inner diameter B may generally be less than 0.0430 inches (0.1092 centimeters), and in some embodiments may be about 0.0420 inches (about 0.1067 centimeters).

Figure 5:
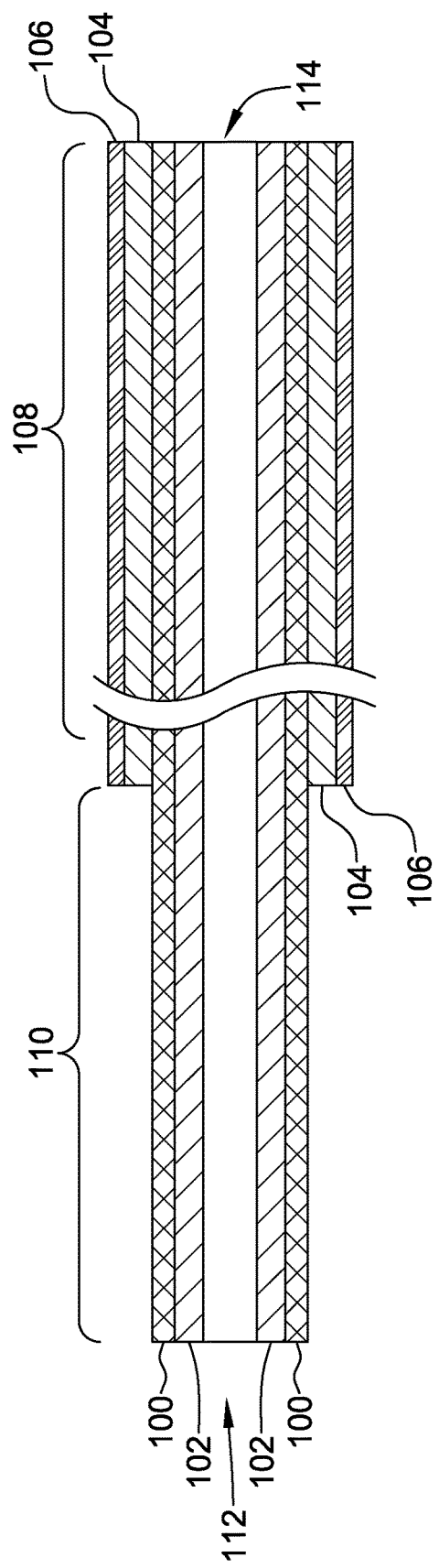
FIG. 5 is longitudinal cross-sectional view of the braided polyimide tube of FIG. 4 showing a portion of the polyimide tube exposed.

Once second outer layer 106 has been introduced onto first outer layer 104, both first outer layer 104 and second outer layer 106 are removed from distal portion 110 of braided polyimide tube 100 beginning at distal end 112; that is, distal portion 110 beginning at distal end 112 of braided polyimide tube 100 is exposed for further processing by removing first outer layer 104 and second outer layer 106. First outer layer 104 and second outer layer 106 may be removed from the distal portion 110 of braided polyimide tube 100 by any suitable means known in the art including for example, chemical etching or laser ablation. Generally, an axial length of from about 3 inches (about 7.62 centimeters) to about 7 inches (about 17.78 centimeters), including from about 4 inches (about 10.16 centimeters) to about 7 inches (about 17.78 centimeters) of first outer layer 104 and second outer layer 106 is removed beginning at distal end 112 of braided polyimide tube 100 and ablating or etching toward proximal end 114 of braided polyimide tube 100. In one particular embodiment, about 3 inches (about 7.62 centimeters) is removed. Referring now to FIG. 5, there is shown braided polyimide tube 100 having first outer layer 104 and second outer layer 106 removed from distal portion 110 of braided polyimide tube 100. First outer layer 104 and second outer layer 106 are still present on proximal portion 108 of braided polyimide tube 100.

After first outer layer 104 and second outer layer 106 have been removed from distal portion 110 of braided polyimide tube 100, distal portion 110 is subjected to a reflow (or other suitable) process to form a new distal portion layer of material on distal portion 110 of braided polyimide tube 100. With a reflow process, a mandrel is first inserted inside of substrate layer 102 to keep the inner diameter constant during manufacturing, and a suitable material is chosen (such as a Pebax® material) and the tubular material pulled over distal section 110 of braided polyimide tube. Once the tube of suitable material is positioned, a heat shrink material is inserted around the tube and a reflow process is completed at a suitable temperature to form a new distal portion layer of material on distal portion 110 of braided polyimide tube 100. When the reflow process is complete, the heat shrink material and mandrel are removed. The new distal portion layer of material on distal portion 110 of braided polyimide tube 100 may have any suitable thickness and may be, for example, about 0.003 inches (about 0.008 centimeters) thick, or even about 0.0035 inches (about 0.0089 centimeters) thick, or even about 0.004 inches (about 0.010 centimeter) thick, or even about 0.005 inches (about 0.0127 centimeters thick). Generally, the thickness of the new distal portion layer on distal portion 110 of braided polyimide tube 100 will have substantially the same thickness as the total thickness of first outer layer 104 and second outer layer 106 on proximal portion 108 of braided polyimide tube 100.

Figure 6:
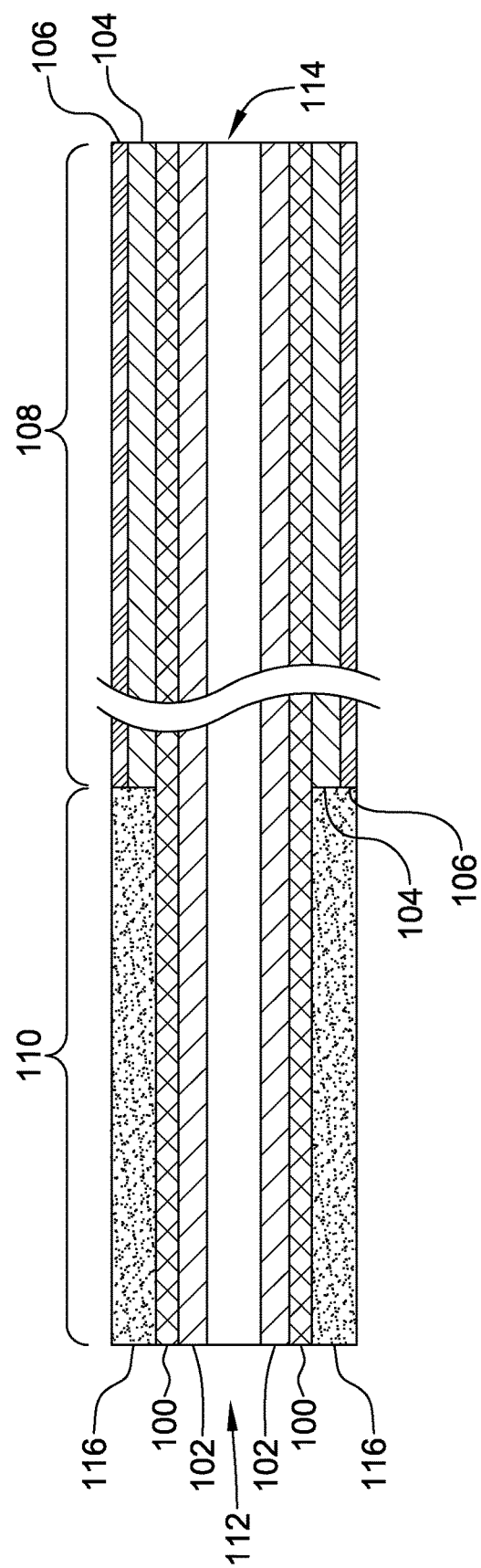
FIG. 6 is a longitudinal cross-sectional view of the braided polyimide tube of FIG. 5 including an additional layer of material on a distal portion.

Referring now to FIG. 6, there is shown braided polyimide tube 100 including first outer layer 104 and second outer layer 106 on proximal portion 108 of braided polyimide tube 100. Also shown is new distal portion layer 116 on distal portion 110 of braided polyimide tube 100. Although any of the materials mentioned above for second outer layer 106 are suitable for materials for constructing new distal portion layer 116 on distal portion 110 of braided polyimide tube 100, polyether block amide (Pebax®) materials have been found to be particularly desirable. In one embodiment, a Pebax® material having a durometer value of about 35 D, about 40 D, about 45 D, or about 55 D is desirable as the material for new distal portion layer 116 on distal portion 110.

After new distal portion layer 116 has been reflowed (or otherwise introduced) onto distal portion 110 of braided polyimide tube 100, a small lengthwise section of distal end 112 of braided polyimide tube 100 may optionally be removed to provide a flush, neat distal end 112 for further processing. The removal or "trim up" of distal end 112 may be accomplished by any means known in the art, including laser ablation or roll cutting with a razor blade. Generally, no more than 0.1 inches (0.254 centimeters), including no more than about 0.025 inches (0.0635 centimeters), of material from distal end 112 is removed during this trim up procedure.

Figure 7:
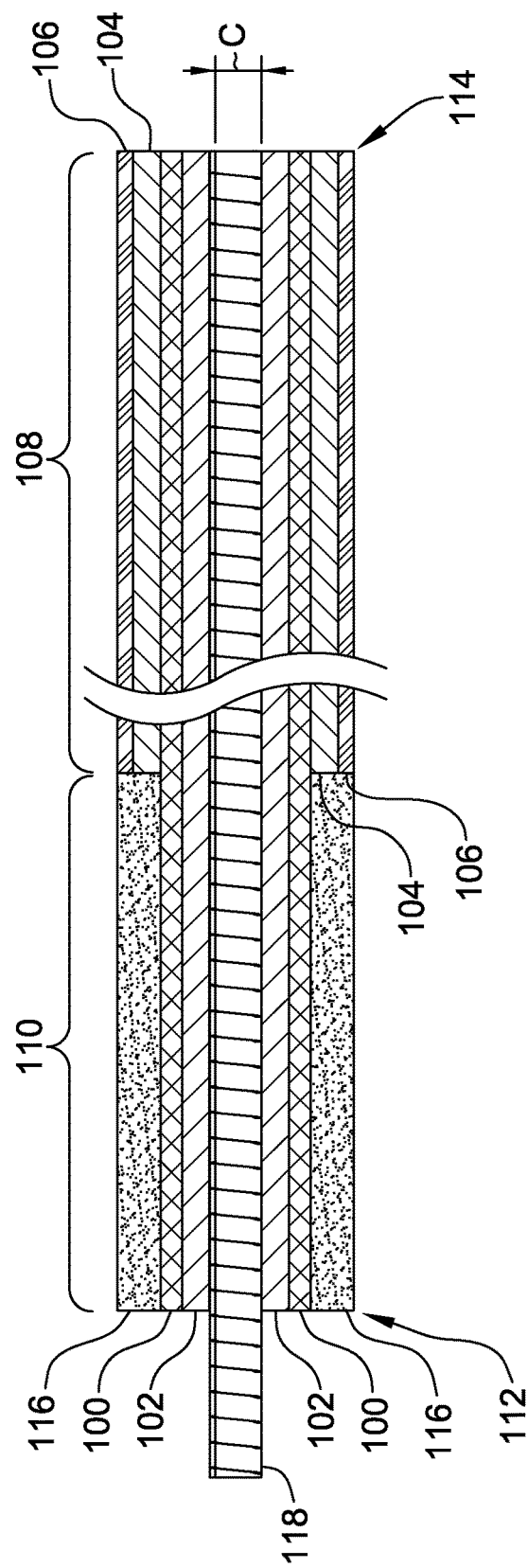
FIG. 7 is a longitudinal cross-sectional view of the braided polyimide tube of FIG. 6 including a spring coil.

Referring now to FIGS. 6 and 7, once new distal portion layer 116 has been deposited onto distal portion 110 of braided polyimide tube 100 (and optionally a trim up done on distal end 112 as described above), spring coil 118 is inserted into the interior of substrate layer 102 and positioned to extend the full length of substrate layer 102 (and hence braided polyimide tube 100) and extend past distal end 112 of braided polyimide tube 100 for further processing. Spring coil 118 may extend past distal end 112 by about 4 inches (about 10.16 centimeters), or even about 3 inches (about 7.62 centimeters), or even about 2.5 inches (about 6.35 centimeters), or even about 2 inches (about 5.08 centimeters), or even about 1.25 inches (about 3.175 centimeters), or even about 1 inch (about 2.54 centimeters) for further processing. In one desirable embodiment, spring coil 118 will extend past distal end 112 by about 2 inches (5.08 centimeters). In another desirable embodiment, spring coil 118 will extend past distal end 112 by about 1.25 inches (about 3.175 centimeters). Spring coil 118 is disposed within substrate layer 102 described above to impart further column strength and kink resistance to braided polyimide tube 100 while maintaining flexibility, and also to minimize slack in the activation wire when the shaft is bent inside the tortuous anatomy. Although spring coil 118 may be disposed within only a portion or portions of substrate layer 102 (i.e., less than the entire length of substrate layer 102), it is generally desirable for spring coil 118 to be disposed within substrate layer 102 such that it runs the entire length of substrate layer 102 and extend past distal end 112. Spring coil 118 has an inner diameter C that may be, for example, less than 0.040 inches (0.102 centimeters), or even less than 0.035 inches (0.089 centimeters), or even less than 0.033 inches (0.084 centimeters), or even less than 0.031 inches (0.078 centimeters). In one desirable embodiment, spring coil 118 has an inner diameter of about 0.030 inches (0.076 centimeters).

Suitable spring coils (also commonly referred to in the art as rigidity compression coils) are well known in the art and commercially available from, for example, Motion Dynamics (Fruitport Charter Township, Mich.). One specific example of a spring coil for use in the present disclosure has an outer diameter of about 0.040 inches (about 0.102 centimeters), an inner diameter of about 0.030 inches (about 0.076 centimeters), and is a rolled flat wire (about 0.0050 inches by about 0.0150 inches) (about 0.013 centimeters by about 0.038 centimeters). Another specific example of a spring coil for use in the present disclosure has an outer diameter of 0.040 inches (about 0.102 centimeters), an inner diameter of about 0.032 inches (0.08128 centimeters), and is a rolled flat wire (about 0.004 inches by about 0.010 inches) (about 0.01016 centimeters by about 0.0254 centimeters). Another specific example of a spring coil for use in the present disclosure has an outer diameter of 0.040 inches (about 0.102 centimeters), an inner diameter of about 0.032 inches (0.08128 centimeters), and is a rolled flat wire (about 0.004 inches by about 0.015 inches) (about 0.01016 centimeters by about 0.038 centimeters). Based on the disclosure herein, one skilled in art will recognize that many other commercially available spring coils may be suitable for use in the present disclosure depending on the desired specific characteristics of the spring coil.

Referring now to FIG. 8, once spring coil 118 has been inserted and positioned inside of substrate layer 102, third outer layer 120 is introduced over spring coil 118. Third outer layer 120 is introduced over spring coil 118 using a suitable reflow (or other) process wherein the desired material, generally in tubular form, is slid over spring coil 118 and a heat shrink material (not shown in FIG. 8) is loaded over the top of the tubular material. A mandrel is inserted within spring coil 118 to hold open the inner diameter and the reflow process done. After the reflow is complete, the heat shrink is removed. As illustrated in FIG. 8, a small length D of spring coil 118 is left uncovered for further processing as described below. Length D may have a length of from about 0.020 inches to about 0.125 inches. Although any of the materials mentioned above for second outer layer 106 are suitable for materials for constructing third outer layer 120 on spring coil 118, Pebax® materials have been found to be particularly desirable. In one embodiment, a Pebax® material having a durometer value of about 35 D, or about 40 D or about 45 D is desirable as the material for third outer layer 120 on spring coil 118. In another embodiment, a Pebax® material having a durometer value of about 55 D is desirable as the material for third outer layer 120 on spring coil 118.

Figure 8A:
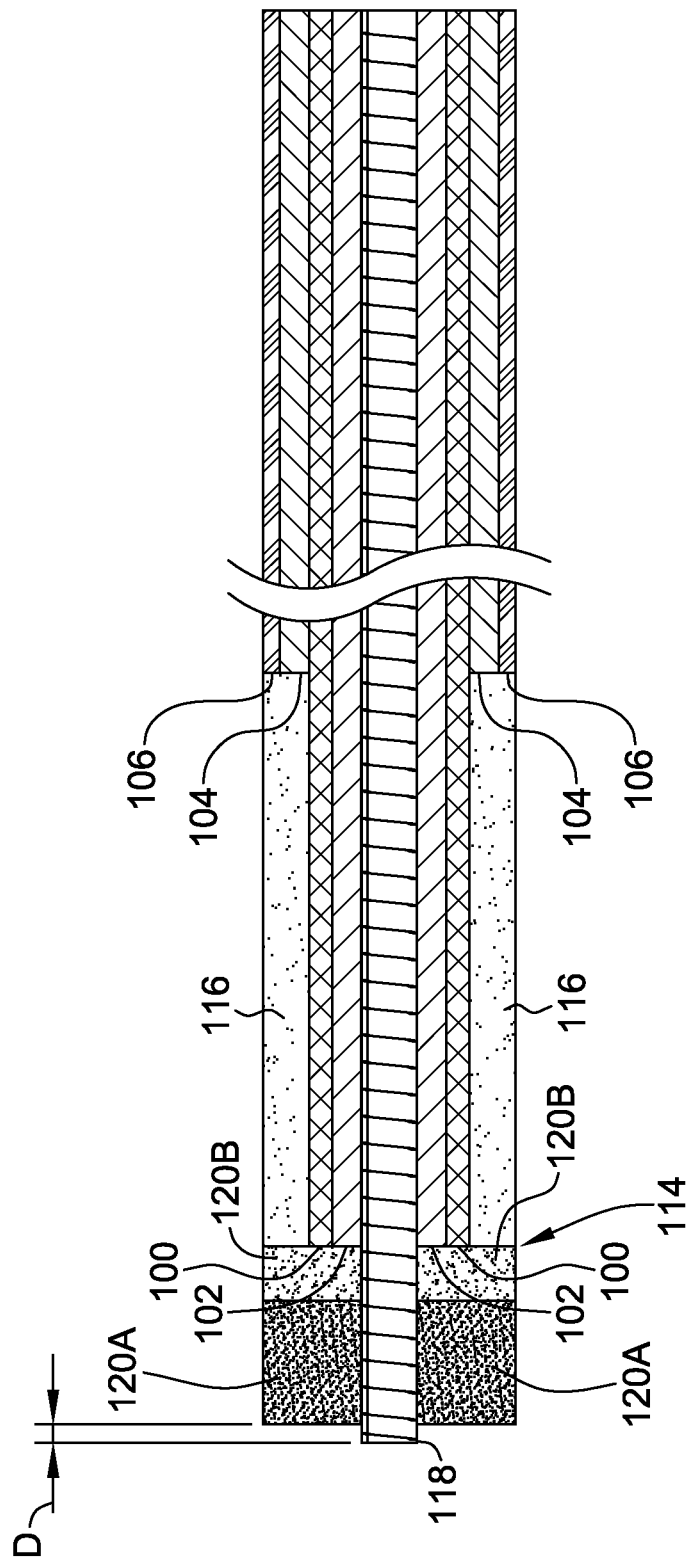

FIG. 8 illustrates third outer layer 120 on spring coil 118 as a single layer, constructed from a single material. In other embodiments of the present disclosure, third outer layer 120 may be constructed of two (or more) materials to impart desirable characteristics to the flexible catheter shaft. This can be accomplished by reflowing two or more different materials onto spring coil 118 as described above. Referring now to FIG. 8A, there is shown an embodiment where spring coil 118 includes third outer layer 120A and third outer layer 120B, wherein third outer layer 120A and third outer layer 120B are constructed from different materials. Any of the materials mentioned above for second outer layer 106 are suitable for materials for constructing third outer layer 120A and third outer layer 120B on spring coil 118. Pebax® materials have been found to be particularly desirable. In one embodiment, a Pebax® material having a durometer value of about 45 D is used to construct third outer layer 120A and a Pebax® material having a durometer value of about 35 D is used to construct third outer layer 120B. The materials used to construct third outer layer 120A and third outer layer 120B may be the same or different as the material used to construct new distal portion layer 116.

Figure 9:
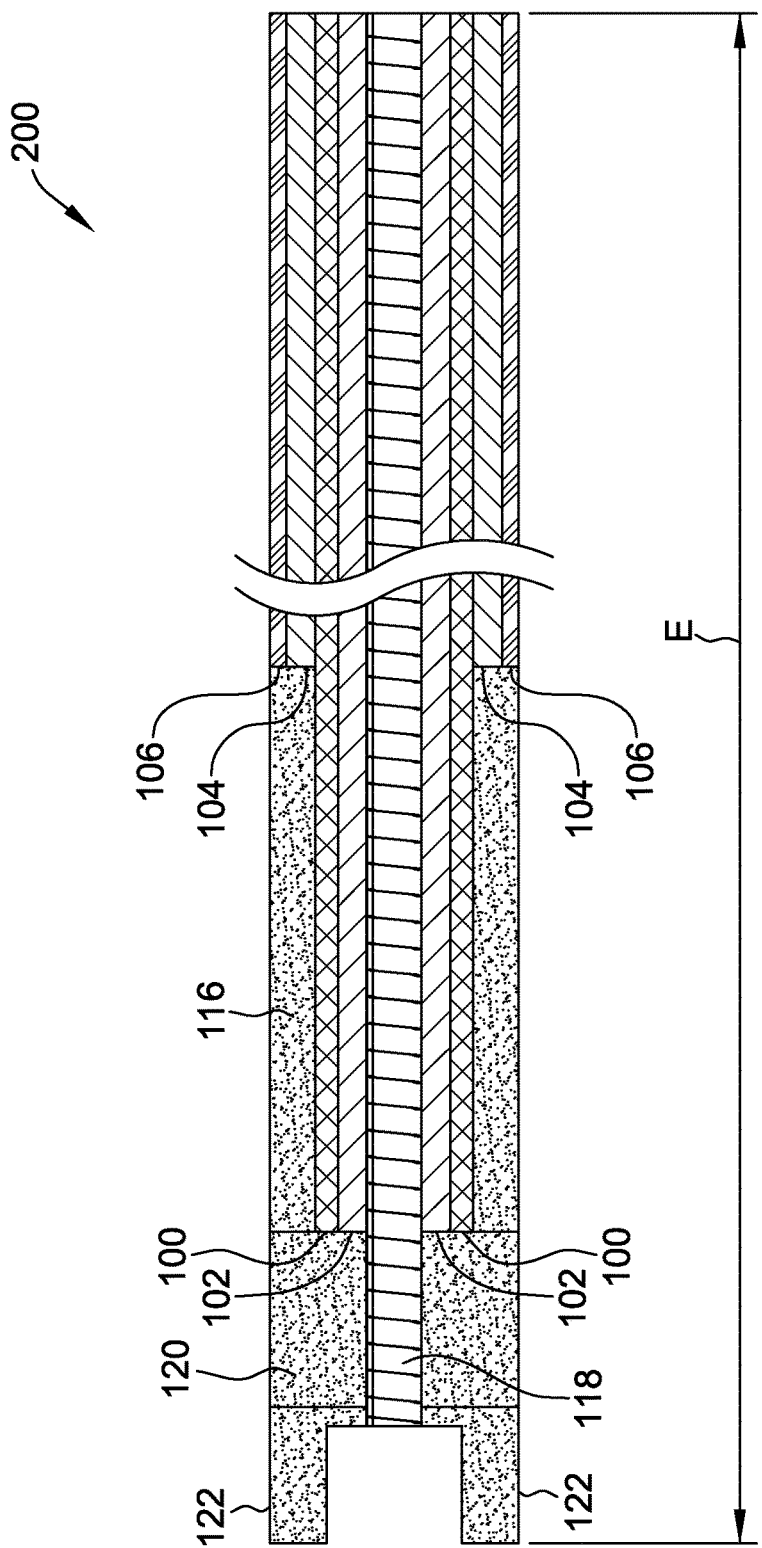
FIG. 9 is a longitudinal cross-sectional view of the braided polyimide tube of FIG. 8 including a pocket on a distal end.

Referring now to FIG. 9, after third outer layer 120 (or third outer layer 120A and 120B) has been introduced on top of spring coil 118, pocket 122 is formed to form flexible catheter shaft 200. Pocket 122 is generally formed using a reflow process where the desired material in tubular form is placed over length D (shown in FIG. 8) of spring coil 118 and a stepped reflow mandrel and wrapped with a heat shrink material. After the reflow process is complete, the stepped reflow mandrel and heat shrink material are removed. Any of the materials mentioned above for second outer layer 106 are suitable for materials for constructing pocket 122. Pebax® materials have been found to be particularly desirable. In one embodiment, a Pebax® material having a durometer value of about 72 D is used to construct pocket 122. Once pocket 122 is formed, flexible catheter shaft 200 will have a length E, as illustrated in FIG. 9. Length E of flexible catheter shaft 200 will generally be from about 20 inches (about 50.8 centimeters) to about 80 inches (about 203.2 centimeters), including from about 30 inches (about 76.2 centimeters) to about 60 inches (152.4 centimeters), including from about 40 inches (about 101.6 centimeters) to about 60 inches (about 152.4 centimeters). In some embodiments, length E may be about 41 inches (about 104.1 centimeters), or about 42 inches (about 106.7 centimeters), or about 43 inches (about 109.22 centimeters) or about 44 inches (about 111.8 centimeters) or even about 45 inches (about 114.3 centimeters). In other embodiments, length E of flexible catheter shaft 200 may be about 60 inches (about 152.4 centimeters) or even about 61 inches (about 154.9 centimeters).

Figure 10:
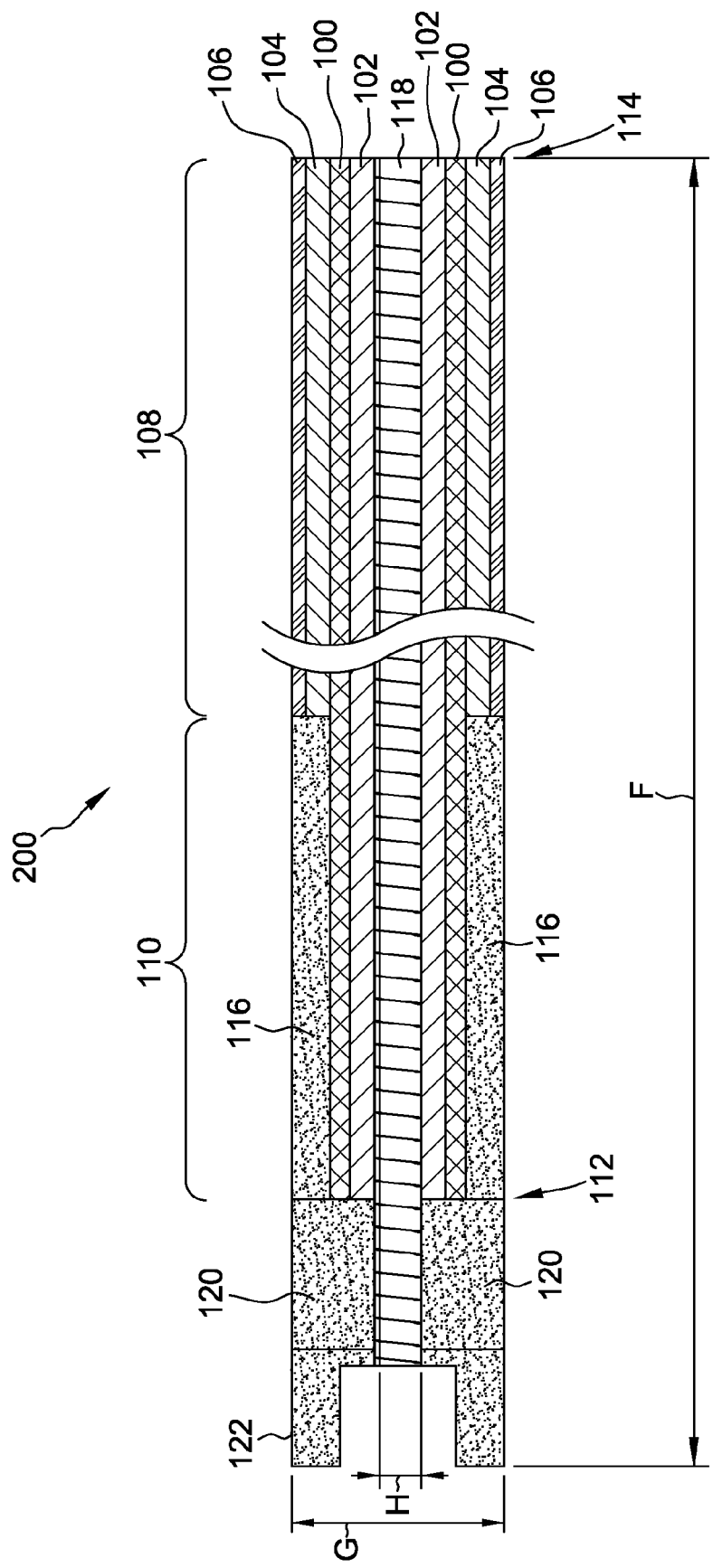
FIGS. 10, 10A, and 10B are cross-sectional longitudinal views of flexible catheter shafts of the present disclosure.

Referring now to FIG. 10, there is illustrated an exemplary flexible catheter shaft 200 in accordance with the present disclosure having a length F, outer diameter G, and inner diameter H. Flexible catheter shaft 200 includes braided polyimide tube 100 having substrate layer 102 disposed therein. Substrate layer 102 has spring coil 118 disposed therein. Braided polyimide tube 100 has proximal portion 108, proximal end 114, distal portion 110, and distal end 112. Braided polyimide tube 100 additionally includes first outer layer 104 and second outer layer 106 on proximal portion 108 of braided polyimide tube 100. Braided polyimide tube 100 also includes new distal portion layer 116. Third outer layer 120 is disposed on spring coil 118, and pocket 122 is partially disposed on spring coil 118. In the embodiment illustrated in FIG. 10, new distal portion layer 116, third outer layer 120, and pocket 122 are shown as being constructed from the same material. In one embodiment similar to that shown in FIG. 10, new distal portion layer 116, third outer layer 120, and pocket 122 may all be constructed from a polyether block amide (Pebax®) material having a durometer value of about 40D; that is, new distal portion layer 116, third outer layer 120, and pocket 122 are all constructed from the same material. In this specific embodiment, length F may be about 43 inches (about 109.2 centimeters), outer diameter G may be about 0.060 inches (about 0.152 centimeters), and inner diameter H may be about 0.030 inches (about 0.077 centimeters).

Figure 10A:
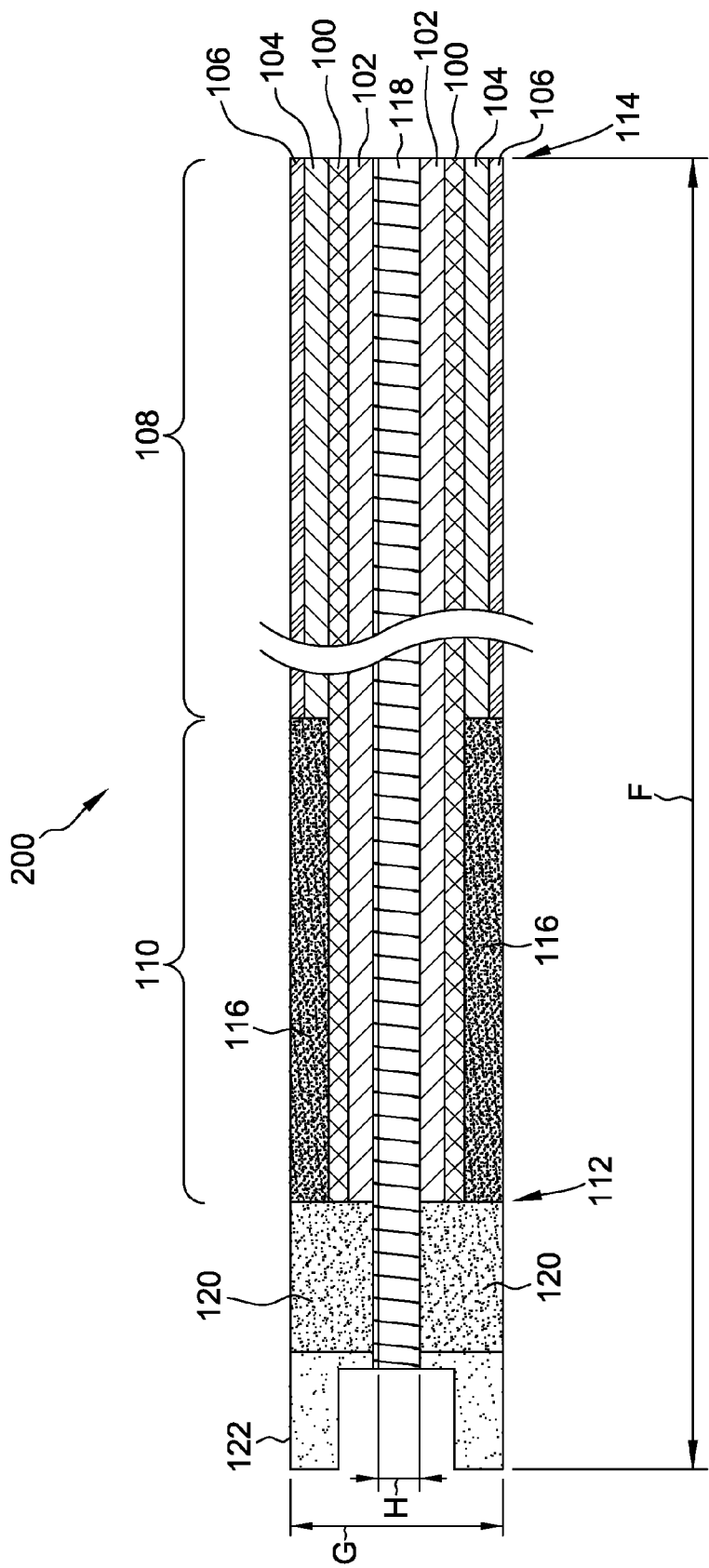

Referring now to FIG. 10A, there is shown another embodiment of flexible catheter shaft 200 of the present disclosure similar to that of FIG. 10. In FIG. 10A, it is shown that new distal portion layer 116, third outer layer 120, and pocket 122 may all be constructed from different materials. Each may be constructed from a polyether block amide (Pebax®) material having a different durometer value. In this specific embodiment, new distal portion layer 116 may be constructed from a polyether block amide (Pebax®) having a durometer value of about 55 D, third outer layer 120 may be constructed from a polyether block amide (Pebax®) having a durometer value of about 40 D, and pocket 122 may be constructed of a polyether block amide (Pebax®) having a durometer value of about 72 D. In this specific embodiment, length F may be about 43 inches (about 109.2 centimeters), outer diameter G may be about 0.060 inches (about 0.152 centimeters), and inner diameter H may be about 0.030 inches (about 0.077 centimeters).

Figure 10B:
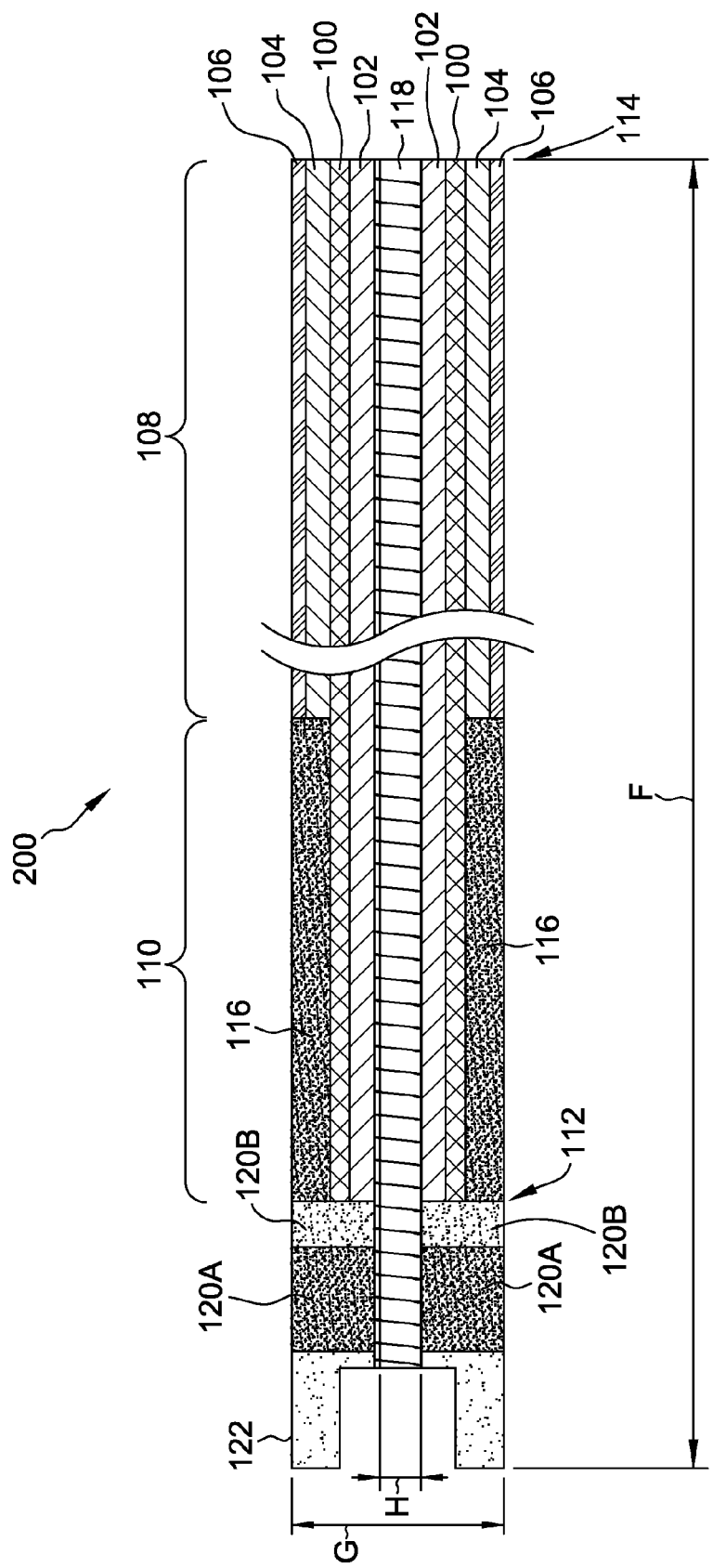

Referring now to FIG. 10B, there is shown another embodiment of flexible catheter shaft 200 of the present disclosure similar to that of FIG. 10. In FIG. 10B, it is shown that new distal portion layer 116 and third outer layer 120A may be constructed from the same material, while third outer layer 120B and pocket 122 are constructed from different materials. Each may be constructed from a polyether block amide (Pebax®) material having a different durometer value. In this specific embodiment, new distal portion layer 116 may be constructed from a polyether block amide (Pebax®) having a durometer value of about 55 D, third outer layer 120A may be constructed from a polyether block amide (Pebax®) having a durometer value of about 55 D, third outer layer 120B may be constructed from a polyether block amide (Pebax®) having a durometer value of about 40 D, and pocket 122 may be constructed of a polyether block amide (Pebax®) having a durometer value of about 72 D. In this specific embodiment, length F may be about 43 inches (about 109.2 centimeters), outer diameter G may be about 0.060 inches (about 0.152 centimeters), and inner diameter H may be about 0.030 inches (about 0.077 centimeters). As one skilled in the art would recognize, the flexible catheter shafts illustrated and described in FIGS. 10, 10A, and 10B are merely exemplary of the present disclosure and many alterations and substitutions of materials could be made within the scope of the present disclosure.

In an alternative embodiment of the present disclosure, a flexible catheter shaft is disclosed that includes a spring coil as described above (such as spring coil 118 as shown in FIG. 7) in combination with an additional outer spring coil on a distal end of the flexible catheter shaft, such that the flexible catheter shaft includes two spring coils as described herein. The additional outer spring coil, which typically is disposed around at least part of spring coil 118 that extends past a distal end of the braided polyimide tube, and in many embodiments around the entire section of spring coil 118 that extends past a distal end of the braided polyimide tube, may be utilized in many embodiments in combination with spring coil 118 to further improve the durability properties of the resulting flexible catheter shaft. In many cases, the addition of the outer spring coil may improve durability by both reducing any potential for layer separation (i.e., reflowed Pebax® layer separation upon flexing and bending of the flexible catheter shaft) and improving the consistency of the outer diameter of an electrode basket upon opening by minimizing slack in pull wire 18 (as shown in FIG. 2).

Figure 11:
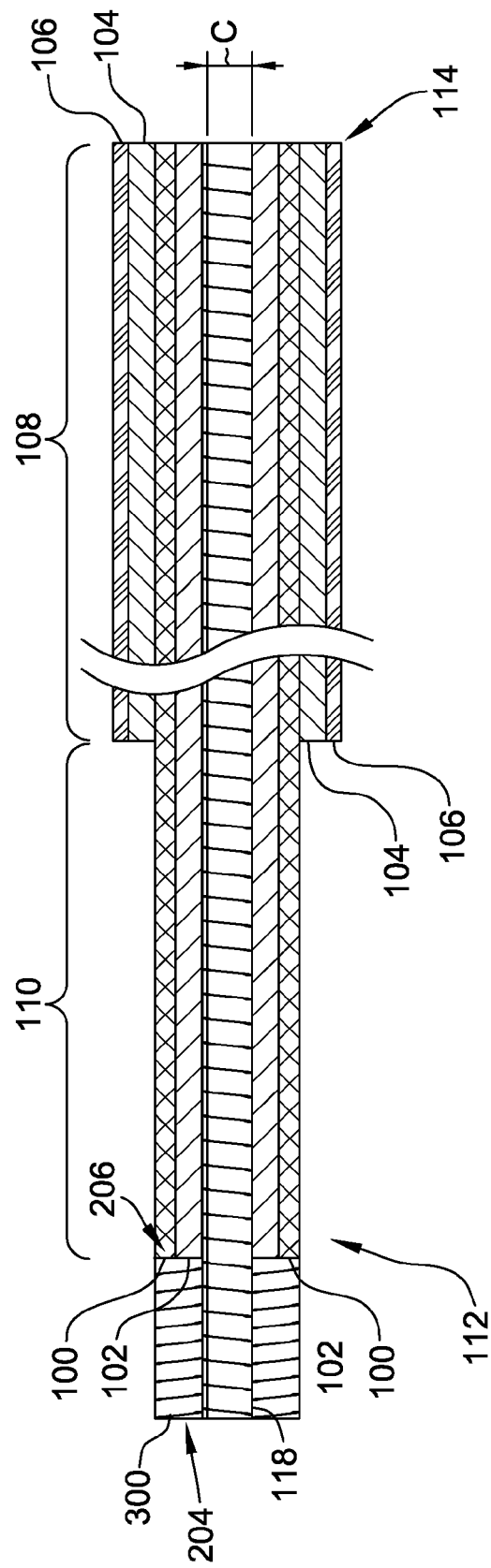
FIG. 11 is a cross-sectional longitudinal view of a flexible catheter shaft of the present disclosure including an outer spring coil.

Referring now to FIG. 11, there is shown braided polyimide tube 100 having substrate layer 102, first outer layer 104, and second outer layer 106. Braided polyimide tube 100 also has proximal portion 108, proximal end 114, distal portion 110, distal end 112, and spring coil 118, positioned to extend the full length of substrate layer 102 (and hence braided polyimide tube 100) and extend past distal end 112 of braided polyimide tube 100. Additionally, outer spring coil 300 is disposed around the portion of spring coil 118 that extends past distal end 112 of braided polyimide tube 100. Outer spring coil 300 has distal end 204 and proximal end 206. As such, in the embodiment shown in FIG. 11, two separate and distinct spring coils are utilized.

Outer spring coil 300 surrounding spring coil 118 may have any inner diameter and outer diameter suitable for use in the flexible catheter shaft such that is fits around spring coil 118 and meshes appropriately as desired with braided polyimide tube 100 and substrate layer 102. In an exemplary embodiment, outer spring coil 300 may have an inner diameter of about 0.042 inches (about 0.107 centimeters) and an outer diameter of about 0.050 inches (about 0.127 centimeters). Although any wind direction of spring coil 300 is within the scope of the present disclosure, in many embodiments outer spring coil 300 will have a wind direction opposite the wind direction of spring coil 118. Suitable outer spring coils may be laser cut from a nitinol tube, stainless steel tube, or may be a wound stainless steel coil with flat ground ends. Suitable outer spring coils are commercially available from, for example, Motion Dynamics (Fruitport Charter Township, Mich.). In some embodiments, the outer spring coil may comprise a zipper pattern, while in other embodiments it may comprise a spiral cut or other suitable pattern to provide desired flexibility and torque properties. It is generally desirable that the outer spring coil be generally flat on the proximal end such that reflowed materials are unable to reach spring coil 118 during further processing and on the distal end so that the reflowed materials is smooth with a consistent outer diameter.

Although it is desirable in many embodiments for outer spring coil 300 to cover the entire portion of spring coil 118 that extends past distal end 112 of braided polyimide tube 100 as shown in FIG. 11, it is within the scope of the present disclosure for outer spring coil 300 to only cover a portion of spring coil 118 that extends past distal end 112 of braided polyimide tube 100.

Figure 12:
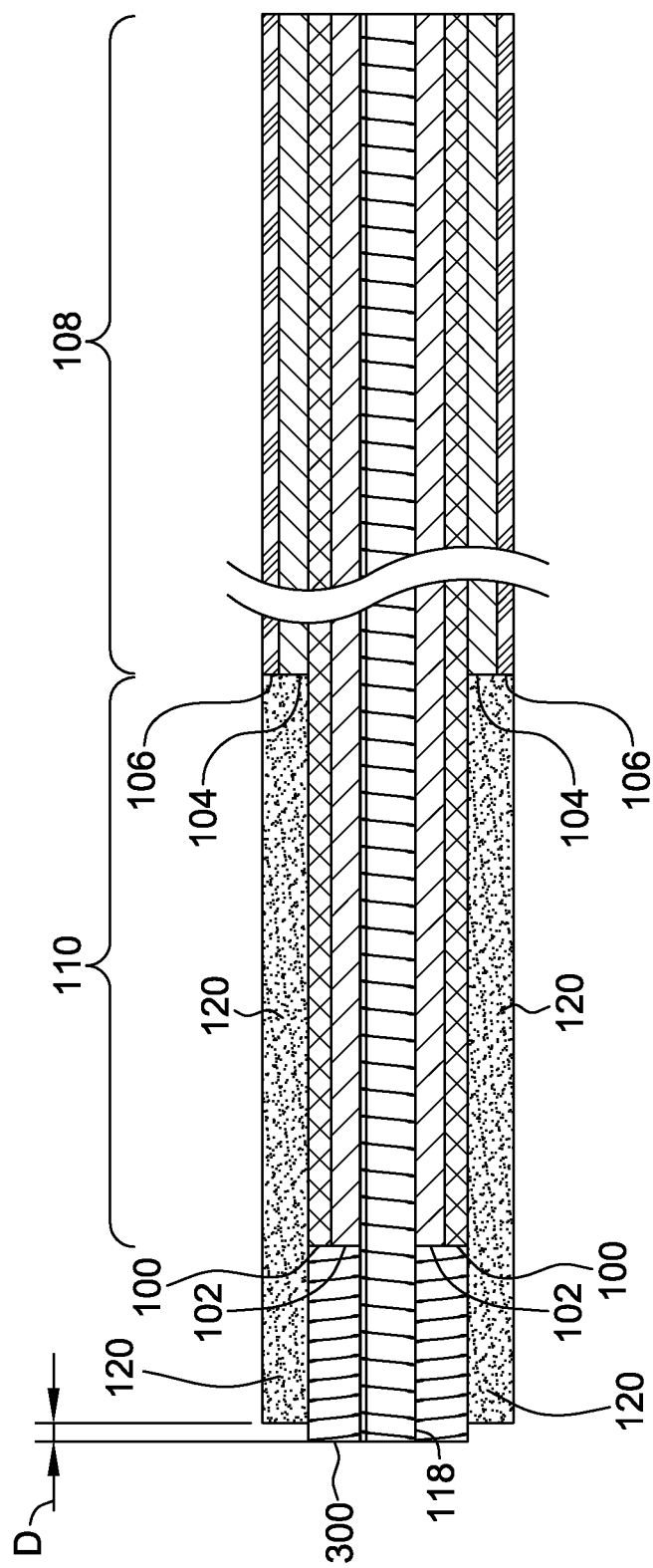
FIG. 12 is a cross-sectional longitudinal view of a flexible catheter shaft of the present disclosure including an outer spring coil and an outer layer comprised of a single material.

Referring now to FIG. 12, once outer spring coil 300 has been positioned around spring coil 118, third outer layer 120 is introduced over distal portion 110 and outer spring coil 300, and hence over spring coil 118. Third outer layer 120 is introduced over distal portion 110 and outer spring coil 300 using a suitable reflow (or other) process wherein the desired material, generally in tubular form, is slid over outer spring coil 300 and distal portion 110 and a heat shrink material (not shown in FIG. 12) is loaded over the top of the tubular material and the reflow process done. After the reflow is complete, the heat shrink is removed. As illustrated in FIG. 12, a small length D of outer spring coil 300 is left uncovered for further processing as described below. Length D may have a length of from about 0.020 inches to about 0.125 inches. Although any of the materials mentioned above for second outer layer 106 are suitable for materials for constructing third outer layer 120 on outer spring coil 300, Pebax® materials have been found to be particularly desirable. In one embodiment, a Pebax® material having a durometer value of about 40 D or about 45 D is desirable as the material for third outer layer 120 on outer spring coil 300. In another embodiment, a Pebax® material having a durometer value of about 55 D is desirable as the material for third outer layer 120 on outer spring coil 300.

Figure 13:
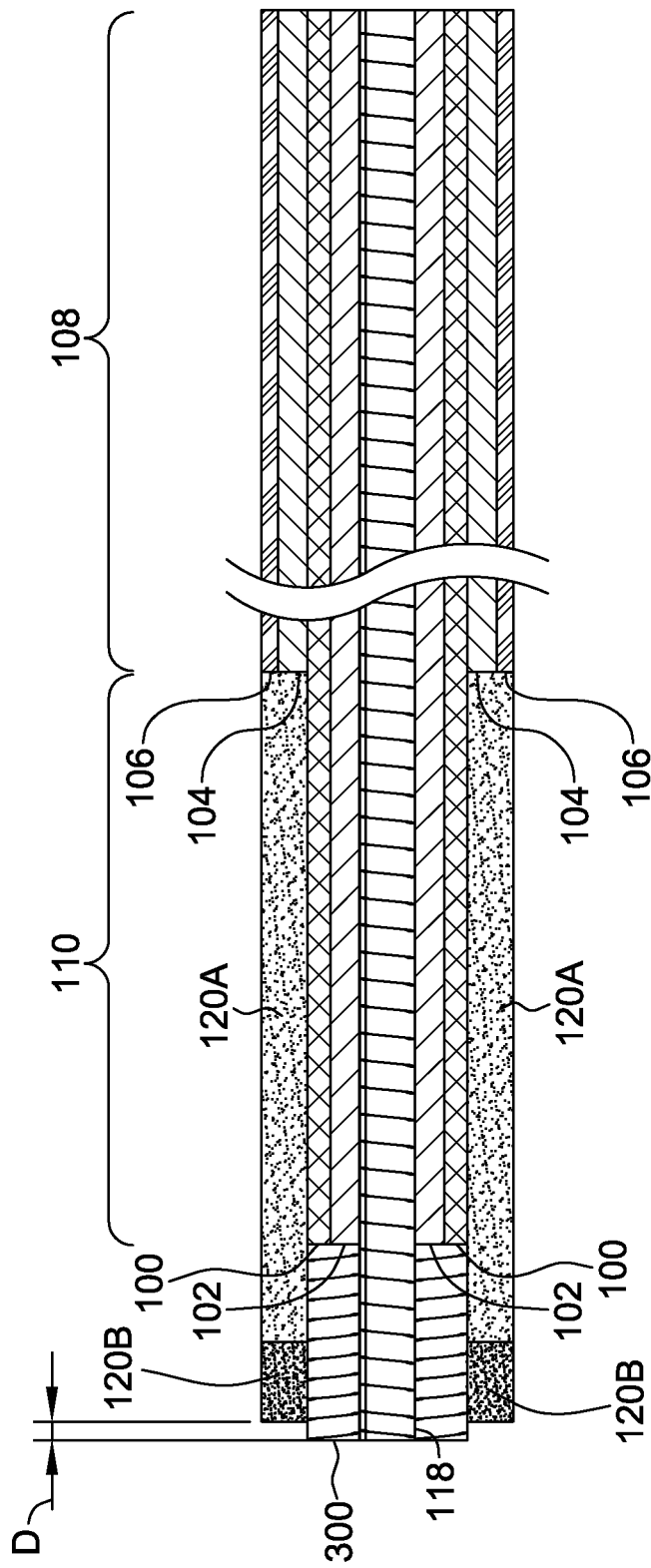
FIG. 13 is a cross-sectional longitudinal view of a flexible catheter shaft of the present disclosure including an outer spring coil and an outer layer comprised a two materials.

FIG. 12 illustrates third outer layer 120 on distal portion 110 and on outer spring coil 300 as a single layer, constructed from a single material. In other embodiments of the present disclosure, third outer layer 120 may be constructed of two (or more) materials to impart desirable characteristics to the flexible catheter shaft. This can be accomplished by reflowing two or more different materials onto distal portion 110 and outer spring coil 300 as described above. Referring now to FIG. 13, there is shown an embodiment where distal portion 110 and outer spring coil 300 include third outer layer 120A and third outer layer 120B, wherein third outer layer 120A and third outer layer 120B are constructed from different materials so as to provide different properties to the flexible catheter shaft. Any of the materials mentioned above for second outer layer 106 are suitable for materials for constructing third outer layer 120A and third outer layer 120B on distal portion 110 and outer spring coil 300. Pebax® materials have been found to be particularly desirable. In one embodiment, a Pebax® material having a durometer value of about 45 D is used to construct third outer layer 120A and a Pebax® material having a durometer value of about 35 D is used to construct third outer layer 120B.

Figure 14:
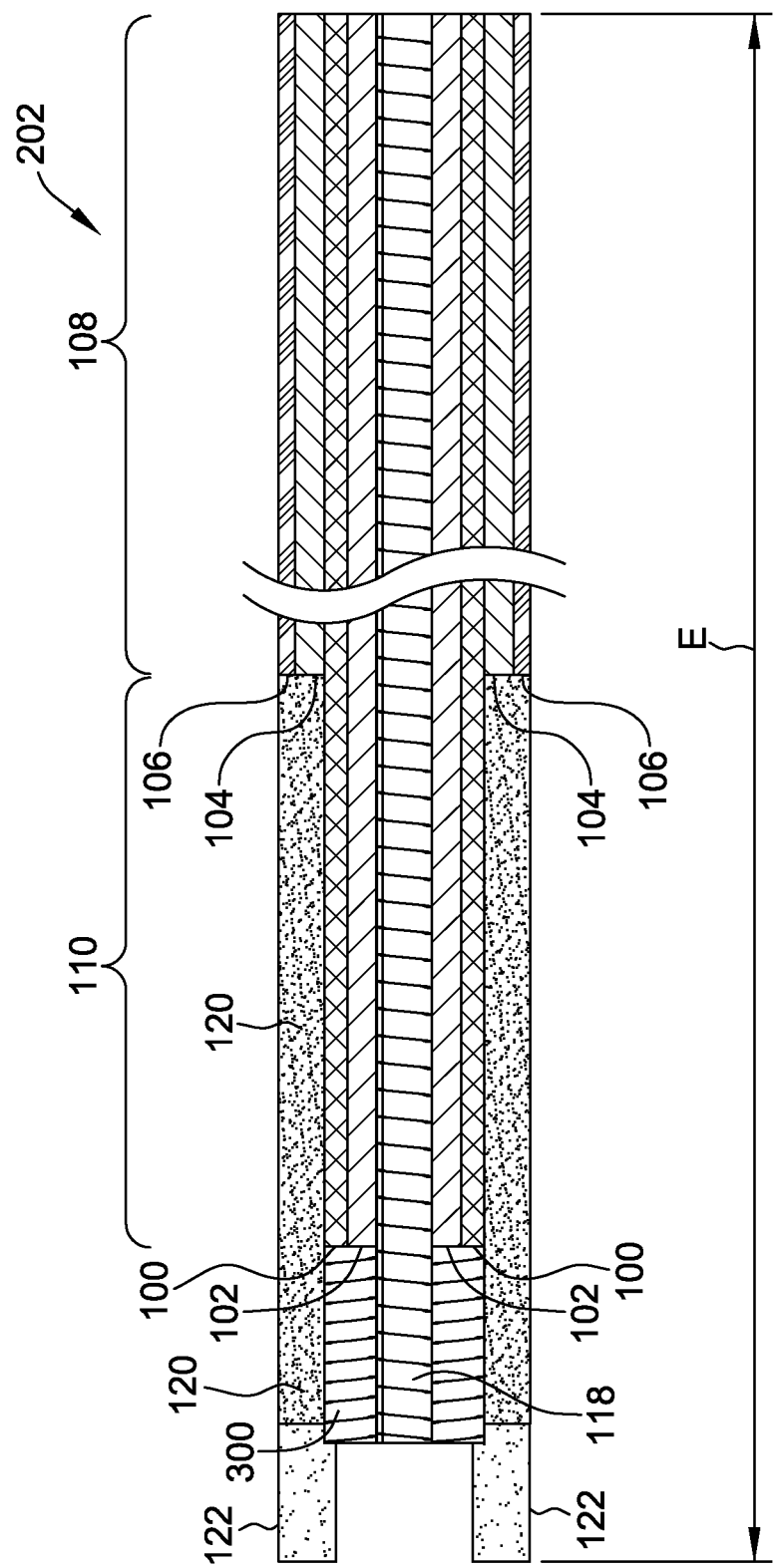
FIGS. 14-17 are various cross-sectional longitudinal views of a flexible catheter shaft of the present disclosure including an outer spring coil, an outer layer, and a pocket on a distal end.

Referring now to FIG. 14, after third outer layer 120 (or third outer layer 120A and 120B as shown in FIG. 13) has been introduced on top of distal portion 110 and outer spring coil 300, pocket 122 is formed to form flexible catheter shaft 202. Pocket 122 is generally formed using a reflow process where the desired material in tubular form is placed over length D (shown in FIGS. 12 and 13) of outer spring coil 300 and a stepped reflow mandrel and wrapped with a heat shrink material. Pocket 122 may be formed from the same or different material as third outer layer 120 (or third outer layer 120A and 120B). After the reflow process is complete, the stepped reflow mandrel and heat shrink material are removed. Any of the materials mentioned above for second outer layer 106 are suitable for materials for constructing pocket 122. Pebax® materials have been found to be particularly desirable. In one embodiment, a Pebax® material having a durometer value of about 72 D is used to construct pocket 122. Once pocket 122 is formed, flexible catheter shaft 202 will have a length E, as illustrated in FIG. 14. Length E of flexible catheter shaft 202 will generally be from about 20 inches (about 50.8 centimeters) to about 80 inches (about 203.2 centimeters), including from about 30 inches (about 76.2 centimeters) to about 60 inches (152.4 centimeters), including from about 40 inches (about 101.6 centimeters) to about 60 inches (about 152.4 centimeters). In some embodiments, length E may be about 41 inches (about 104.1 centimeters), or about 42 inches (about 106.7 centimeters), or about 43 inches (about 109.22 centimeters) or about 44 inches (about 111.8 centimeters) or even about 45 inches (about 114.3 centimeters). In other embodiments, length E of flexible catheter shaft 202 may be about 60 inches (about 152.4 centimeters) or even about 61 inches (about 154.9 centimeters).

Figure 15:
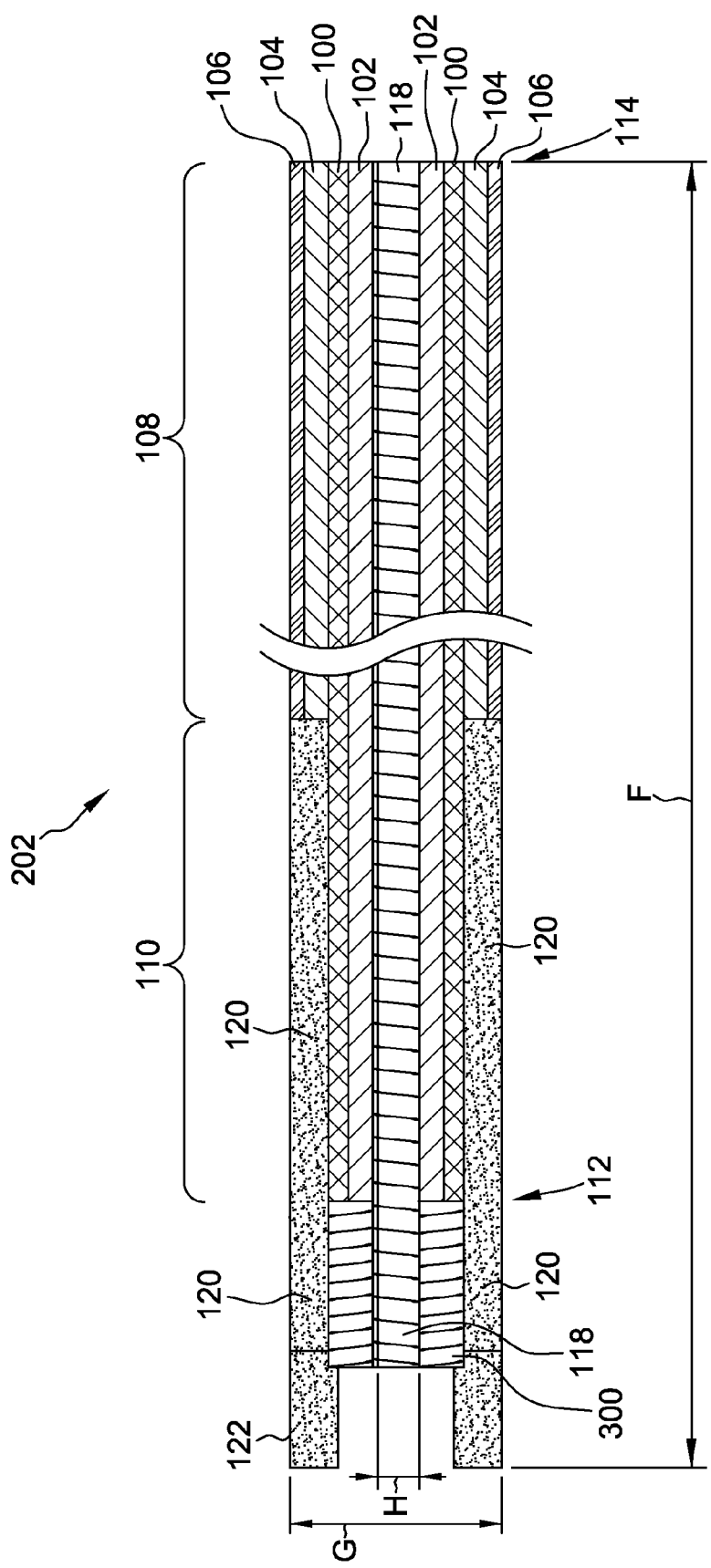

Referring now to FIG. 15, there is illustrated an exemplary flexible catheter shaft 202 in accordance with the present disclosure having a length F, outer diameter G, and inner diameter H. Flexible catheter shaft 202 includes braided polyimide tube 100 having substrate layer 102 disposed therein. Substrate layer 102 has spring coil 118 disposed therein. Braided polyimide tube 100 has proximal portion 108, proximal end 114, distal portion 110, and distal end 112. Braided polyimide tube 100 additionally includes first outer layer 104 and second outer layer 106 on proximal portion 108 of braided polyimide tube 100. Braided polyimide tube 100 also includes third outer layer 120. Third outer layer 120 is also disposed on outer spring coil 300, and pocket 122 is partially disposed on outer spring coil 300. In the embodiment illustrated in FIG. 15, third outer layer 120 and pocket 122 are shown as being constructed from the same material. In one embodiment third outer layer 120 and pocket 122 may be constructed from a polyether block amide (Pebax®) material having a durometer value of about 40 D; that is, third outer layer 120 and pocket 122 are both constructed from the same material. In this specific embodiment, length F may be about 43 inches (about 109.2 centimeters), outer diameter G may be about 0.060 inches (about 0.152 centimeters), and inner diameter H may be about 0.030 inches (about 0.077 centimeters).

Figure 16:
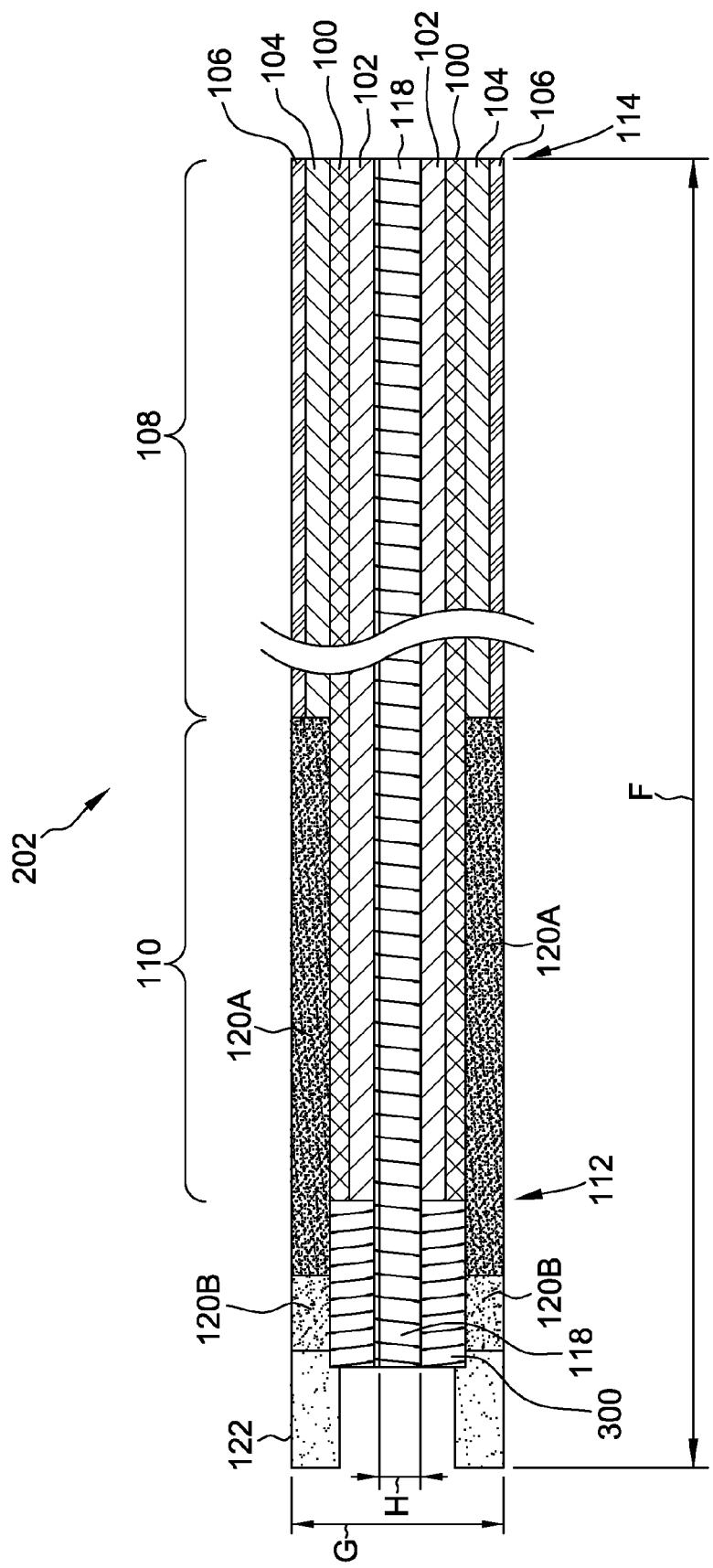

Referring now to FIG. 16, there is shown another embodiment of flexible catheter shaft 202 of the present disclosure where it is shown that third outer layer 120A and 120B and pocket 122 may all be constructed from different materials. Each may be constructed from a polyether block amide (Pebax®) material having a different durometer value. In this specific embodiment, third outer layer 120A may be constructed from a polyether block amide (Pebax®) having a durometer value of about 55 D, third outer layer 120B may be constructed from a polyether block amide (Pebax®) having a durometer value of about 40 D, and pocket 122 may be constructed of a polyether block amide (Pebax®) having a durometer value of about 72 D. In this specific embodiment, length F may be about 43 inches (about 109.2 centimeters), outer diameter G may be about 0.060 inches (about 0.152 centimeters), and inner diameter H may be about 0.030 inches (about 0.077 centimeters).

Figure 17:
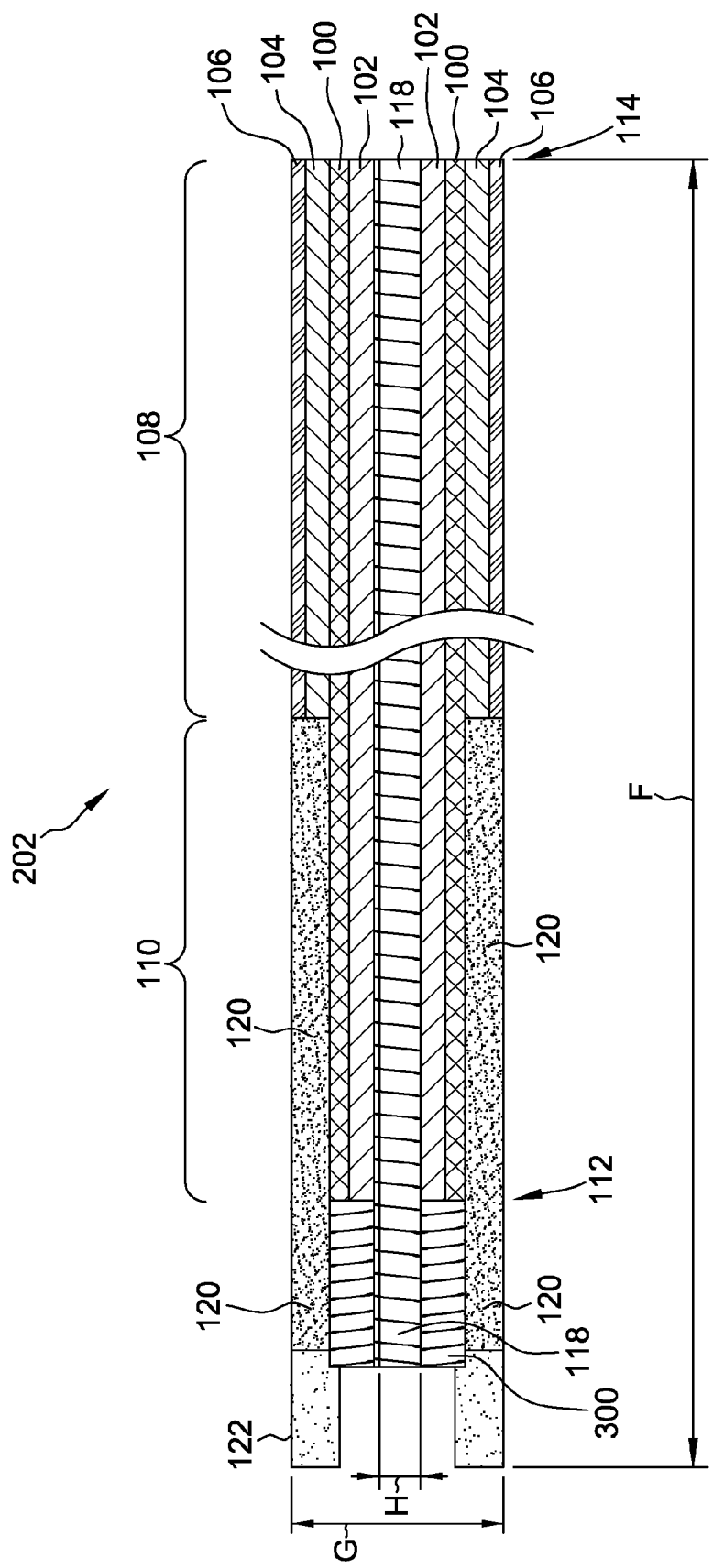

Referring now to FIG. 17, there is shown another embodiment of flexible catheter shaft 202 of the present disclosure. In FIG. 17, it is shown that third outer layer 120 and pocket 122 may be constructed from different materials. Each may be constructed from a polyether block amide (Pebax®) material having a different durometer value. In this specific embodiment, third outer layer 120 may be constructed from a polyether block amide (Pebax®) having a durometer value of about 45 D and pocket 122 may be constructed of a polyether block amide (Pebax®) having a durometer value of about 72 D. In this specific embodiment, length F may be about 43 inches (about 109.2 centimeters), outer diameter G may be about 0.060 inches (about 0.152 centimeters), and inner diameter H may be about 0.030 inches (about 0.077 centimeters). As one skilled in the art would recognize, the flexible catheter shafts illustrated and described in the various Figures are merely exemplary of the present disclosure and many alterations and substitutions of materials could be made within the scope of the present disclosure.

As noted above, in many embodiments of the present disclosure, the flexible catheter shaft is sized and configured to allow for easy insertion through a 6 French guide catheter and to allow a contrast agent to be passed between the flexible catheter shaft and guide catheter during a procedure. Although generally sized and configured for insertion through a 6 French guide catheter, the flexible catheter may be sized and configured for insertion through other sized guide catheters in accordance with the present disclosure.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A catheter shaft comprising a braided polyimide tube having a proximal portion, a distal portion and a tip; wherein the tip is a distalmost end of the braided polyimide tube; the distal portion extending from the proximal portion to the tip of the braided polyimide tube, a substrate layer disposed within the braided polyimide tube, and a spring coil disposed within the substrate layer and including a section extending past the tip of the braided polyimide tube, wherein the proximal portion of the braided polyimide tube is covered by a first coating, wherein the distal portion of the braided polyimide tube is covered by a second coating, wherein the section of the spring coil that extends past the tip of the braided polyimide tube is covered by a third coating, wherein a pocket surrounds a distal portion of the spring coil and extends distally past a distal end of the spring coil, the pocket having an outer diameter larger than an outer diameter of the braided polyimide tube, and wherein the pocket is configured for receiving at least a portion of an electrode basket therein.

2. The catheter shaft of claim 1 wherein the braided polyimide tube comprises stainless steel reinforcing strands selected from the group consisting of flat wires, round wires, and combinations thereof.

3. The catheter shaft of claim 1 wherein the braided polyimide tube comprises 0.001 inch by 0.003 inch flat wire stainless steel strands.

4. The catheter shaft of claim 1 wherein substrate layer comprises a material selected from the group consisting of a polytetrafluoroethylene/polyimide composite material, a polyimide material, a polytetrafluoroethylene material, and combinations thereof.

5. The catheter shaft of claim 1 wherein the spring coil is a flat wound coil having an inner diameter of about 0.030 inches.

6. The catheter shaft of claim 1 wherein the first coating covering the proximal portion of the braided polyimide tube comprises a first layer and a second layer covering the first layer.

7. The catheter shaft of claim 1 wherein the second coating covering the distal portion of the braided polyimide tube comprises a single layer comprising a polyether block amide material.

8. The catheter shaft of claim 1 wherein the third coating covering the section of the spring coil that extends past the distalmost end of the braided polyimide tube comprises at least one polyether block amide material.

* * * * *